US009323238B2

(12) United States Patent
Buckenham

(10) Patent No.: US 9,323,238 B2
(45) Date of Patent: Apr. 26, 2016

(54) BIOENERGY STORAGE AND MANAGEMENT SYSTEM AND METHOD

(71) Applicant: N. Ross Buckenham, Dallas, TX (US)

(72) Inventor: N. Ross Buckenham, Dallas, TX (US)

( * ) Notice: Subject to any disclaimer, the term of this patent is extended or adjusted under 35 U.S.C. 154(b) by 0 days.

(21) Appl. No.: 14/452,246

(22) Filed: Aug. 5, 2014

(65) Prior Publication Data

US 2016/0041538 A1   Feb. 11, 2016

(51) Int. Cl.
  *G05B 15/02*  (2006.01)
  *C12M 1/107*  (2006.01)
  *C12M 1/00*  (2006.01)
  *H02K 7/18*  (2006.01)

(52) U.S. Cl.
  CPC .............. *G05B 15/02* (2013.01); *C12M 21/04* (2013.01); *C12M 43/04* (2013.01); *C12M 43/08* (2013.01); *H02K 7/18* (2013.01)

(58) Field of Classification Search
  CPC ...... G05B 15/02; C12M 43/08; C12M 43/04; C12M 21/04; H02K 7/18
  See application file for complete search history.

(56) References Cited

U.S. PATENT DOCUMENTS

| 2002/0114866 | A1* | 8/2002 | Kartchner | A23J 1/003 426/55 |
| 2005/0120715 | A1* | 6/2005 | Labrador | F01K 27/00 60/618 |
| 2007/0254196 | A1* | 11/2007 | Richards | F01D 15/10 60/39.281 |
| 2010/0105127 | A1* | 4/2010 | Ginsburg | C02F 11/04 435/262 |
| 2010/0148585 | A1* | 6/2010 | Adam | F02C 3/20 307/66 |
| 2011/0126601 | A1* | 6/2011 | Bottcher | C05F 11/02 71/10 |
| 2013/0024014 | A1* | 1/2013 | Sharma | G05B 13/04 700/29 |
| 2013/0073098 | A1* | 3/2013 | Gan | H02J 3/32 700/286 |
| 2013/0122575 | A1* | 5/2013 | Revankar Krishna Prasad | C12M 21/12 436/287.1 |
| 2013/0238158 | A1* | 9/2013 | Gan | G06Q 10/04 700/295 |
| 2013/0252120 | A1* | 9/2013 | Robertson | H01M 8/0656 429/418 |
| 2014/0015323 | A1* | 1/2014 | Matthews | H02J 4/00 307/52 |
| 2014/0039708 | A1* | 2/2014 | Curtis | F02D 25/00 700/288 |
| 2014/0352332 | A1* | 12/2014 | Mann | F17C 13/025 62/48.1 |

* cited by examiner

*Primary Examiner* — Ramesh Patel
(74) *Attorney, Agent, or Firm* — David W. Carstens; Sudhakar V. Allada; Carstens & Cahoon, LLP

(57) ABSTRACT

A bioenergy management system and method for generating and supplying on-demand auxiliary electrical power is disclosed. The system/method includes a biogas generation unit (BGU) that produces biogas from dairy farm manure and stores the biogas in a biogas storage unit (BSU). An stored energy electric generation unit (SEGU) converts the stored biogas to electricity. A biogas control unit (BCU) measures the quality and quantity of biogas stored in the BSU and calculates available electric power (AEP) from this information. Depending on auxiliary electrical power requirements, a utility control unit (UCU) initiates an on-demand request for electric power (REP) to the BCU using a producer communication device (PCD)/utility communication device (UCD) data link. The BCU processes the REP from the UCU and negotiates electrical power (NEP) quantity. The BCU may electrically connect the SEGU to an electric transmission grid (ETG) to allow instantaneous/scheduled NEP delivery to the ETG.

30 Claims, 16 Drawing Sheets

Time of the Day
0211

*Prior Art*

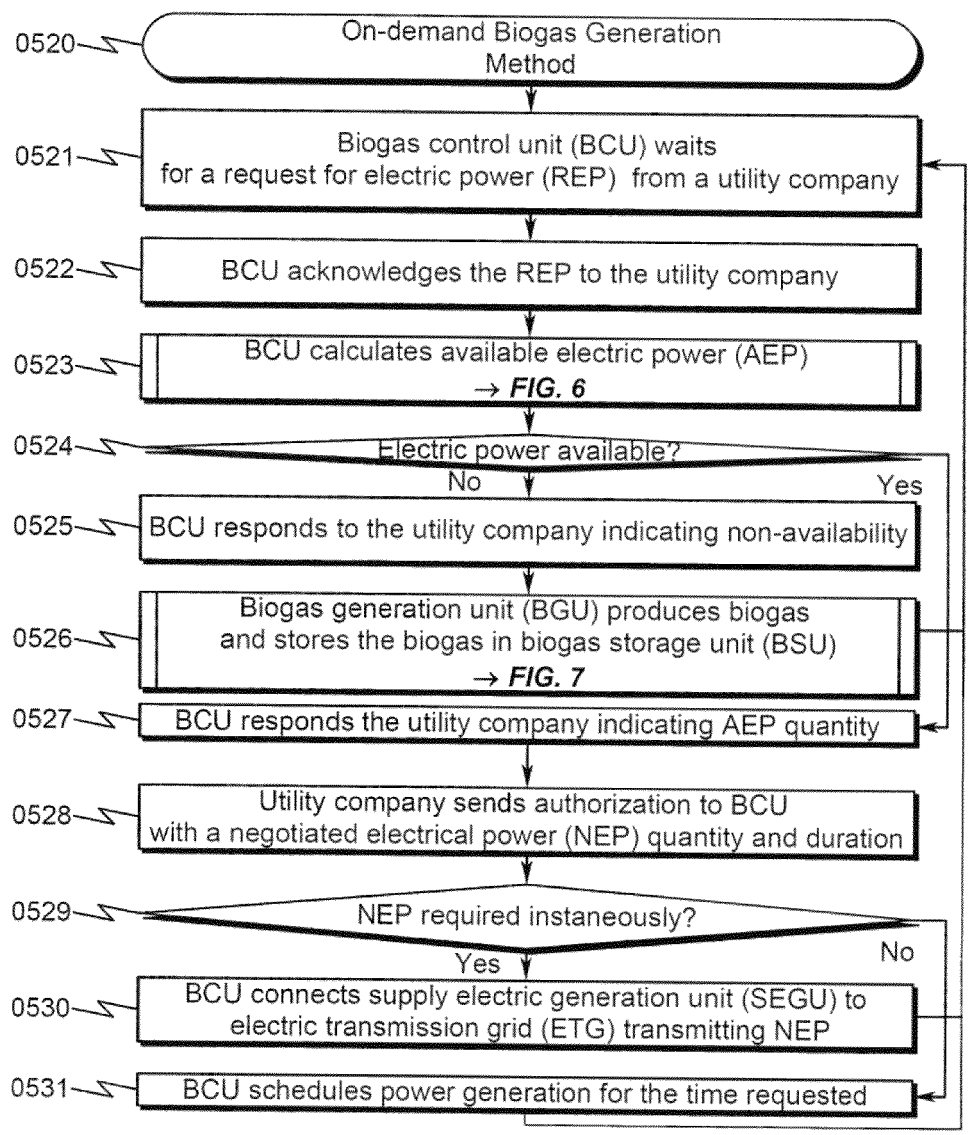

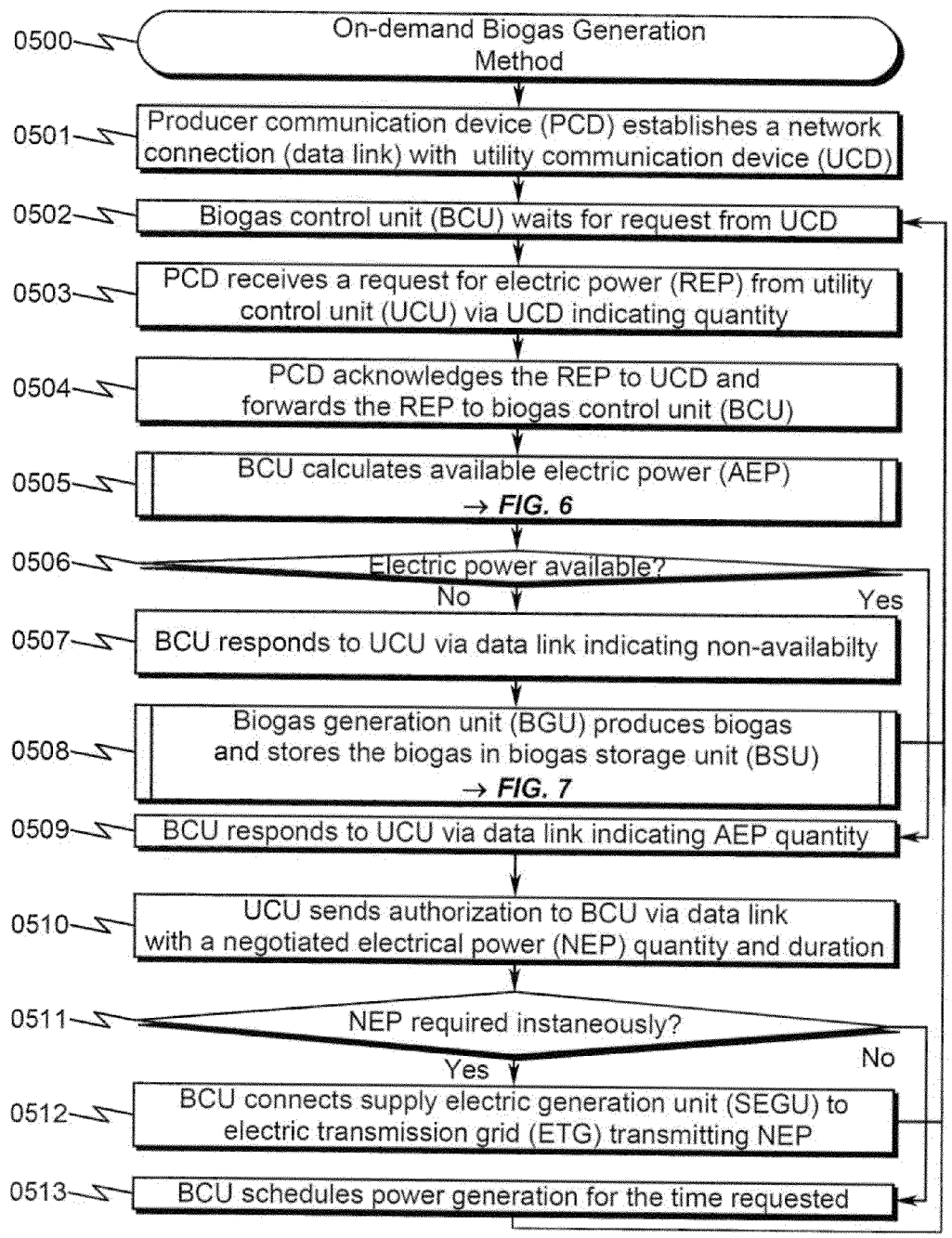

BIOENERGY STORAGE AND MANAGEMENT SYSTEM AND METHOD

CROSS REFERENCE TO RELATED APPLICATIONS

Not Applicable

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to bioenergy generation, storage and management. Specifically, the invention attempts to meet renewable energy demand through bioenergy generation and storage, specifically from methane gas production from organic materials including food and animal waste.

PRIOR ART AND BACKGROUND OF THE INVENTION

Prior Art Background

Over the years, consumers have learned to expect electricity on demand from power plants that run on coal, natural gas or oil. But these fossil fuels, which provide reliable, around-the-clock energy, also emit so called greenhouse gas that may contribute to global warming.

Renewable energy is electricity generated by fuel sources that restore themselves over a short period of time and do not diminish. Although some renewable energy technologies have an impact on the environment, renewables are considered environmentally preferable to conventional sources and, when replacing fossil fuels, have significant potential to reduce greenhouse gas emissions. Some of the mainstream renewable technologies include wind power, solar energy, hydropower, geothermal energy and biomass. Environmental and economic benefits of renewable energy include generating energy that produces no greenhouse gas emissions from fossil fuels, reduction in air pollution, diversifying energy supply, and reducing dependence on fossil fuels.

Many states have encouraged and supported renewable energy generation through various incentives. One such incentive is a Renewable Portfolio Standard (RPS) that requires utility companies to obtain a certain percentage of their electricity from renewable sources. Some states like California require 30% of total energy to be generated from renewable sources by 2020. While wind power and solar energy contribute a big portion of the renewable energy, they are intermittent resources and are not base-load or dispatchable. They rely on sunshine and wind which depend on environmental conditions that are not easily predictable nor controllable. Therefore, there is a need for a more reliable renewable energy source that can generate electrical power round-the-clock and/or on-demand regardless of weather conditions or renewable fuel availability.

In addition, given the intermittent nature of most renewable energy resources and their increasingly important roll in the energy mix, there is significant need for renewable energy storage systems that will allow independent system operators (ISO's), such as the CA ISO, to move the delivery renewable energy to times in the day when it is most needed rather than when it is produced.

In addition, there is a need for an electric control system such as a smart grid, that uses information and communications technology to gather and act on information, such as information about the behaviors of suppliers/producers and consumers, in an automated fashion to improve the efficiency, reliability, economics, and sustainability of the production and distribution of renewable electricity. Information that flows back and forth from the suppliers and utility company may aid in balancing the load on the grid that may prevent voltage fluctuations.

Prior Art System Overview (0100)

As generally seen in the system diagram of FIG. 1 (0100), prior art systems associated with renewable energy management may include a solar energy unit (0101) and a wind energy unit (0102) connected to an electric transmission line (0103) that supplies electricity to a transmission substation (0104). Substation (0104) may distribute power to other distribution substations that then distribute power to residences and industries using distribution lines. Solar energy unit (0101) and wind energy unit (0202) may also connect to a distribution sub substation (0105) that supplies electrical power to transmission lines (0103).

Solar energy unit (0101) may convert solar energy into electricity in one of two ways: using photovoltaic cells, which turn the sun's light into electricity using a semiconductor material that absorbs photons and releases electrons; or using solar-thermal turbines, which use the sun's heat to generate steam, which then spins a turbine to produce electricity.

The big problem with solar power is that the sun does not shine all the time. At nighttime or on cloudy days, solar power plants cannot access the solar energy and thus cannot be relied upon to deliver power during these times of the day. When a cloud floats overhead, the plant may be at an energy standstill, suddenly delivering only a small portion of its rated output. Without energy storage solar-generated power is thus unavailable many hours of the day, and especially not available, for example, during the evening, when power demand is significant.

Wind energy unit (0102) may include turbines that can be as tall as a 20-story building and have three 200-foot-long (60-meter-long) blades. The wind spins the blades, which turn a shaft connected to a generator that produces electricity. Wind energy, like solar, is also an intermittent resource. A sudden modest drop in wind speed can produce a sudden and significantly greater drop in energy production. Producing energy storage for wind power to smooth out the production has been one of the key challenges of the wind industry. So far, the solution has been to attempt to use lithium-ion battery systems, fly wheels or pumped hydro systems to store wind energy, all of which have proven to be very expensive.

Utilities utilize fossil fuel powered generation facilities powering them up and down as needed to fill in the gaps between the supply from these intermittent resources and the demand.

Hydro and geothermal renewable energy sources are more predictable, dispatch-able and base-load like but there is limited additional availability of these resources resulting in much of the expanded RPS goals being met with the other intermittent renewable energy sources.

In order to meet the renewable energy requirements i.e., as defined by the RPS values set by certain states, electric utility companies have come to significantly depend on wind turbines (0102) and solar energy (0101). Solar energy is one of the predominant sources of renewable energy but due to its time of day delivery profile substantial quantities of Solar energy coming onto the grid during the afternoons is causing grid stability issues and delivering excessively during the afternoons and insufficiently during other times of the day. As utility companies strive to meet higher RPS standards they are finding the need to deploy and rely on "stored energy" systems to smooth out the delivery and bridge the gaps caused from the significant percent of overall energy coming from intermittent, non-base-load and non-dispatch-able renewable resources such as wind turbines an solar systems. Storing energy generated from wind or solar may require energy storage infrastructure which has historically not been cost efficient. Therefore, there is a need for additional and new innovative renewable energy storage resources that can store renewable energy for a period of time and that can be used to deliver and/or generate electricity when demanded by an electric utility company.

Prior Art Renewable Energy Management Chart (0200)

As generally seen in the chart of FIG. 2a (0200), power and energy output from prior art associated with renewable energy generation is plotted against time of the day. X-axis (0201) shows the time of the day and Y-axis (0202) shows total renewable available electric power production. In most cases, total renewable available electric power is primarily a combination of wind energy and solar energy. As seen from FIG. 2, available renewable electric power production may start for example at 7.5% during night and early part of the day when there is no sunshine. Available electric power may rise to 30% or more (and a growing %) of demand during the afternoon hours when the solar energy is at its peak. As seen in FIG. 2a, (0213) shows shortage of renewable energy during night and early hours of the day and potentially an excess of renewable energy in the afternoons.

In addition, Independent System Operators (ISO's) and Public Utility Commissions in states such as California where RPS goals are high and renewable energy is becoming significant have initiated major energy storage procurement programs because of the so called "Duck Curve" problem (FIG. 2b). A grid stability problem (Duck Curve) arises as the amount of solar energy coming onto the grid in the afternoons causes too high of a dependency on intermittent renewable resources. Without renewable energy storage, the more reliable fossil fuel plants must power down to accommodate the influx of intermittent power flowing onto the grid. This causes rising grid instability during these times as the base load generators that historically provide grid frequency synchronization go off line. As shown in FIG. 2b, the Duck Curve problem is projected to become significantly worse over the next several years especially as shown from 2015 to 2020. Therefore, there is a need to store renewable energy when it is in excess supply.

Deficiencies in the Prior Art

The prior art as detailed above suffers from the following deficiencies:
- Prior art systems do not provide for reliable renewable energy sources that can generate electrical power round-the-clock or on-demand regardless of weather conditions.
- Prior art systems do not provide for reliable renewable energy sources that can be stored for a period of time and generate electricity when demanded by an electric utility company.
- Prior art renewable energy systems do not provide for complementing currently available renewable energy sources to meet state policies for obtaining a certain percentage of electric power from renewable sources without using batteries or low efficiency energy storage systems such as fly wheels or compressed air.
- Prior art systems do not provide for communication between renewable energy sources and utility companies in an automated fashion to manage a stored renewable energy resource to improve efficiencies and grid stability.

While some of the prior art may teach some solutions to several of these problems, the core issue of storing renewable energy and generating electric power using renewable sources has not been effectively addressed by prior art.

OBJECTIVES OF THE INVENTION

Accordingly, the objectives of the present invention are (among others) to circumvent the deficiencies in the prior art and affect the following objectives:
(1) Provide for reliable renewable energy sources that can generate electrical power round-the-clock, or on-demand regardless of weather or solar conditions.
(2) Provide for reliable renewable energy sources that can store renewable energy for a period of time and use this stored energy to generate electricity when required or demanded by an electric utility company.
(3) Provide for complementing currently available renewable energy sources to meet state policies for obtaining a certain percentage of electric power from renewable sources.
(4) Provide a means to (simultaneously generate and) store renewable energy in form of bio-methane or biogas, produced at one time for use at another time, coupled with a means to convert this stored energy into electricity when needed or when required by a utility or ISO.
(5) Provide for communication between renewable energy sources and utility companies in an automated fashion to improve efficiencies.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

System Overview

The present invention in various embodiments addresses one or more of the above objectives in the following manner. The present invention provides a system to store bioenergy and generate electricity on-demand. The system includes a biogas generation unit (BGU) that produces biogas from dairy farm manure or other organic sources and stores the biogas in a biogas storage unit (BSU). A stored energy electric generation unit (SEGU) that converts the stored renewable energy in the form of biogas to electricity. A biogas control unit (BCU) measures the quality and/or quantity of biogas stored in the BSU and calculates available electric power (AEP) from this information. Depending on auxiliary electrical power requirements, a utility control unit (UCU) initiates an on-demand request for electric power (REP) to the BCU using a producer communication device (PCD)/utility communication device (UCD) data link. In a preferred exemplary embodiment the REP may be communicated by an electric utility company to a biogas producer via a phone call. The BCU ensures sufficient stored energy is available to meet contracted energy storage amounts and obligations and allows excess biogas to be vented, flared or used to generate electrical power via a generator not controllable by the UCU. The BCU ensures that after energy delivery is requested by the UCU that biogas is no longer vented, flared or consumed by other devices in excessive amounts until such time as the energy storage system has been re-charged to its contract storage level. The BCU processes the REP from the UCU and delivers electrical power (NEP) quantity. The BCU may electrically connect the SEGU to an electric transmission grid (ETG) to allow immediate or scheduled NEP delivery to the ETG. Alternatively the SEGU may deliver NEP to an on-site consumer in a "behind the meter" mode of operation where the SEGU is not connected to a UCD but is controlled by programmable logic in the BCU.

Method Overview

The present invention system may be utilized in the context of an overall bioenergy management method, wherein the bioenergy management system described previously is controlled by a method having the following steps:
(1) with said BCU, waiting for a request for electrical power (REP) indicating quantity (power level and duration) from a utility company;
(2) with said BCU, acknowledging said REP to said utility company;
(3) with said BCU, calculating available electrical energy and power (AEP) from said stored biogas;
(4) with said BCU, determining if said AEP is greater than 0, and if so, proceeding to step (7);
(5) with said BCU, responding with non-availability to said utility company;
(6) with said BGU, generating biogas and proceeding to said step (1);
(7) with said BCU, responding with said AEP quantity to said utility company;
(8) with said utility company, sending authorization to said BCU, for a negotiated electrical power (NEP) that is less than or equal to said AEP;
(9) with said BCU, determining if said NEP is required instantaneously, and if not, proceeding to step (11);
(10) with said BCU, connecting said SEGU to said ETG, transmitting said NEP and proceeding to said step (1); and
(11) with said BCU, connecting said SEGU to the ETG at a scheduled time, transmitting said NEP and proceeding to said step (1).

Integration of this and other preferred exemplary embodiment methods in conjunction with a variety of preferred exemplary embodiment systems described herein in anticipation by the overall scope of the present invention.

BRIEF DESCRIPTION OF THE DRAWINGS

For a fuller understanding of the advantages provided by the invention, reference should be made to the following detailed description together with the accompanying drawings wherein:

FIG. 5 illustrates an exemplary overview flowchart describing a presently preferred embodiment of the present invention.

FIG. 5a illustrates an exemplary biogas storage automatic communication flowchart describing a presently preferred embodiment of the present invention.

DESCRIPTION OF THE PRESENTLY PREFERRED EXEMPLARY EMBODIMENTS

Figure 1:
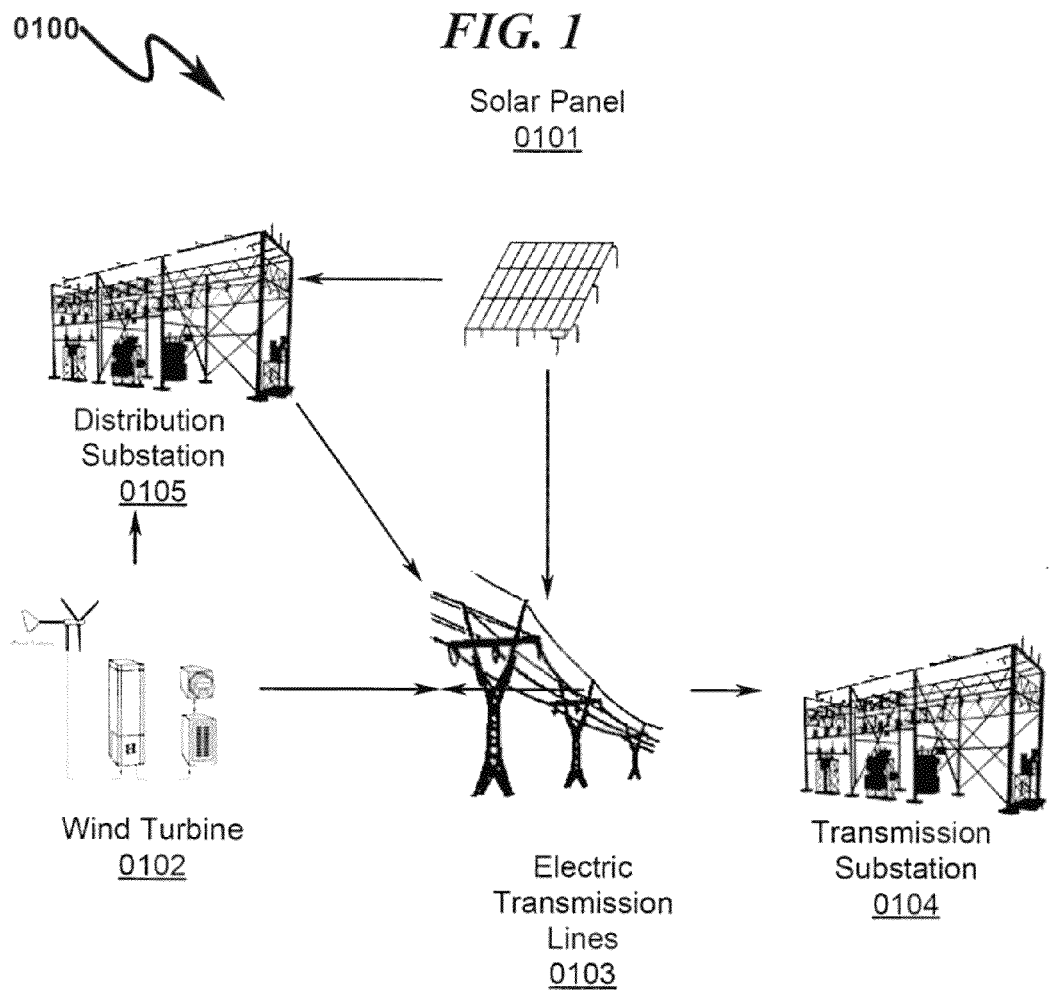
FIG. 1 illustrates a system block overview diagram describing how prior art systems approach bioenergy management.
Figure 2A:
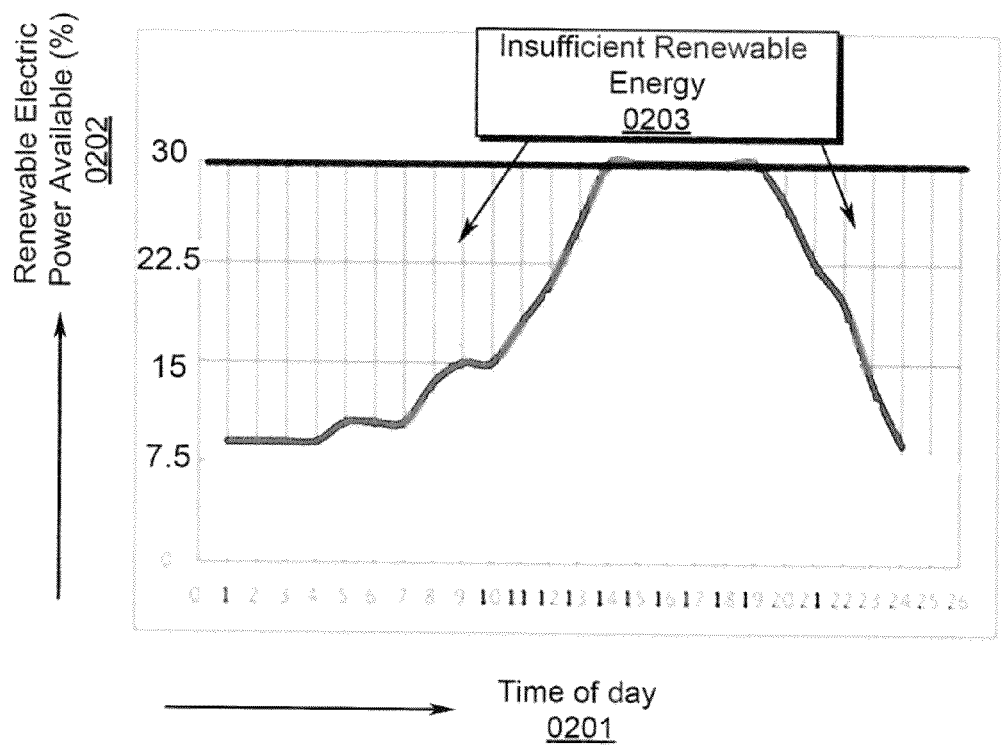
FIG. 2a illustrates a graph describing how prior art systems manage renewable energy.
Figure 2B:
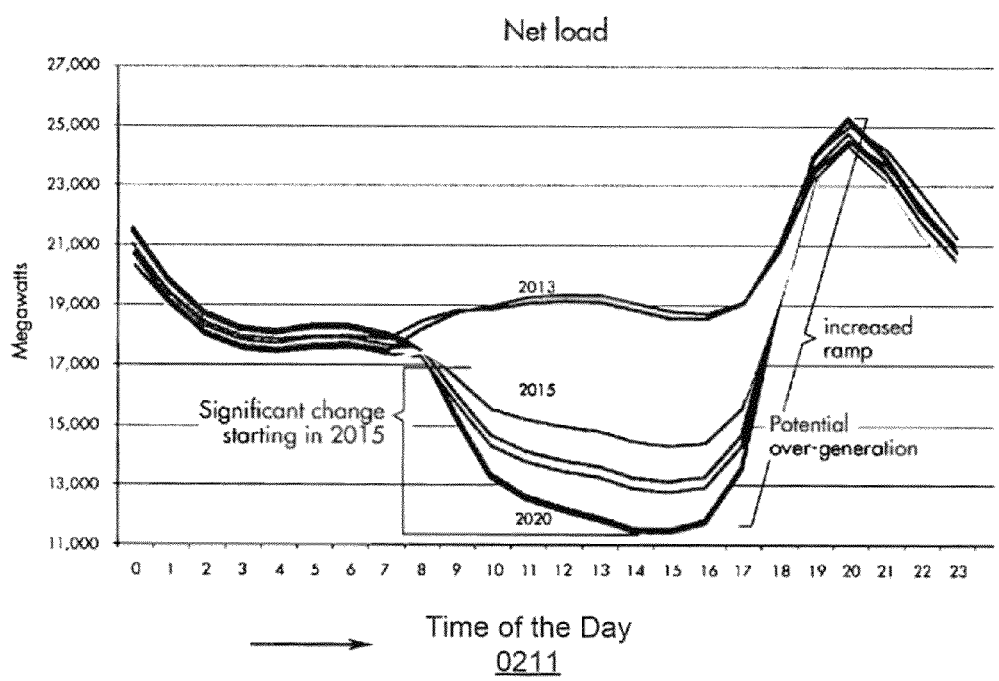
FIG. 2b shows a graph ("Duck Curve") describing how prior art systems can destabilize the energy grid and fail to manage renewable energy without renewable energy storage.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a bioenergy management system and method. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Preferred Embodiment System Block Diagram (0350)

Figure 3A:
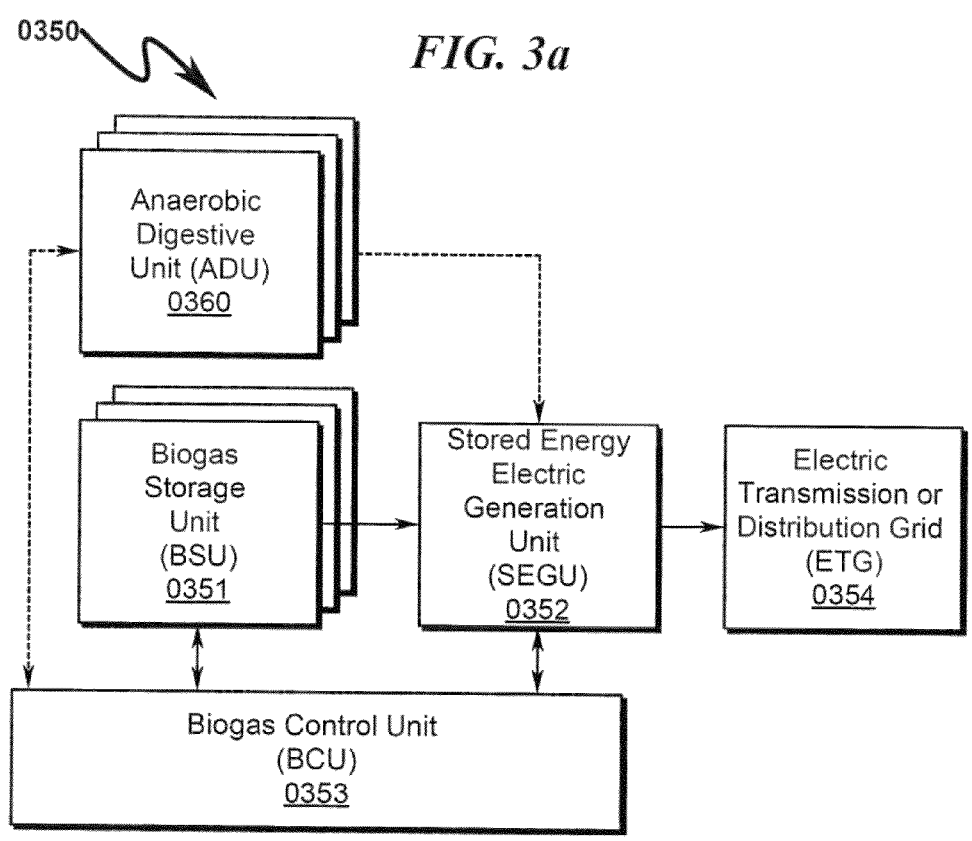
FIG. 3a illustrates an exemplary system block overview describing a presently preferred embodiment of the present invention.

The present invention may be seen in more detail as generally illustrated in FIG. 3a (0350), wherein a biogas storage unit (BSU) (0351) is in fluid communication with a stored energy electrical generation unit (SEGU) (0352). According to a preferred exemplary embodiment, plural BSUs (0351) may be in fluid communication with the SEGU (0352).

The BSU(s) (0351) may be configured to transfer biogas to SEGU (0352) using a conduit large enough for safe and efficient transfer. The conduit may be controlled by auxiliary control systems and valves. The BSU(s) (0351) may be connected to a biogas generation unit (BGU) that further comprises operational units as described below in FIG. 4. In a preferred exemplary embodiment, the BGU may be configured to connect to SEGU (0352) directly to supply biogas. The SEGU (0352) further comprises operational units that are described below in FIG. 10. In some cases, when BSU(s) (0301) and SEGU (0352) are separated by long distances, a pump or blower may be used to transfer the biogas. Additionally, manual storage equipment may also be used to transport the biogas.

Figure 11:
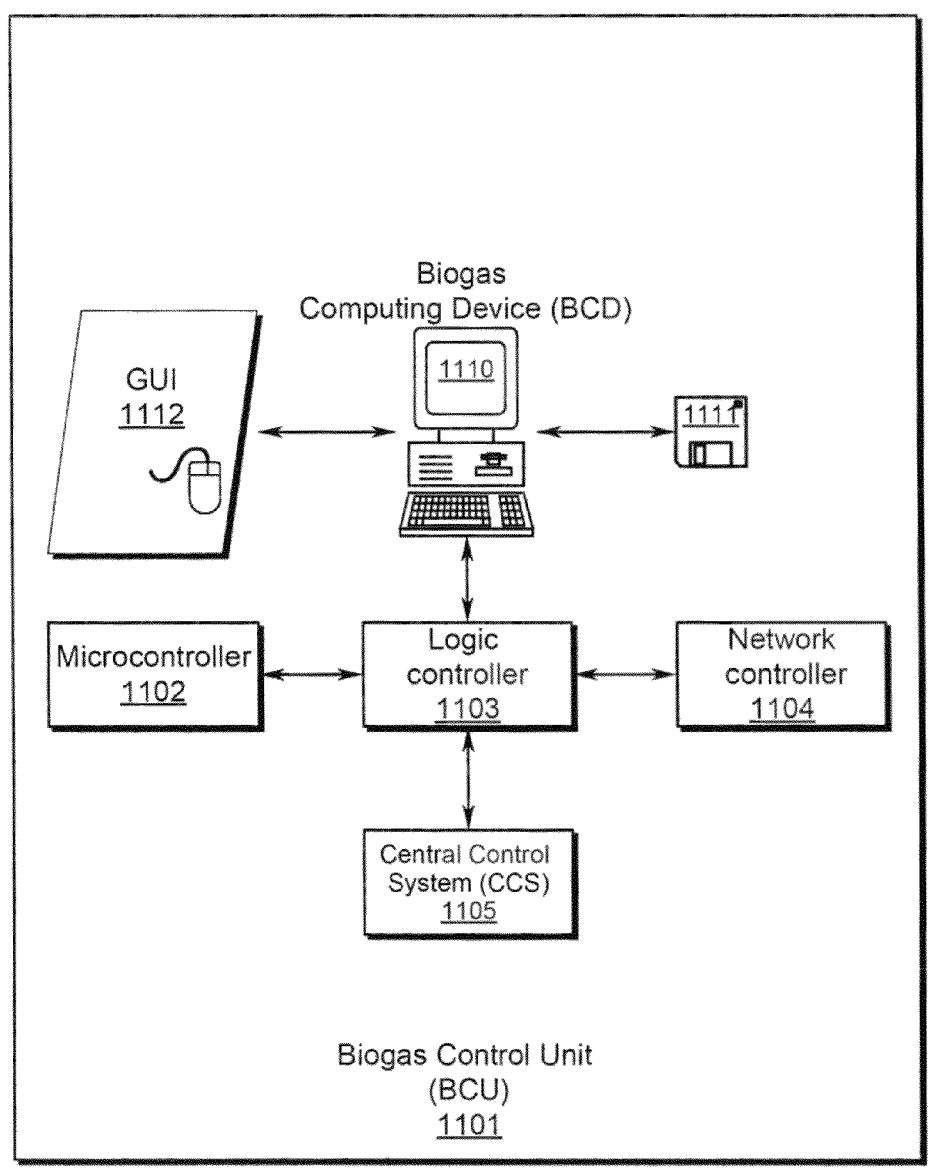
FIG. 11 illustrates an exemplary block diagram of a preferred exemplary biogas control unit (BCU) embodiment.

A biogas control unit (BCU) (0353) may be electronically coupled to the BSU(s) (0351) and the SEGU (0352). The BCU (0353) may use analog or digital electronic signals to control remote units and sensors. A user may invoke an automated process using a graphical user interface (GUI) on BCU (0353). FIG. 11 as generally described below, further provides additional details for the BCU (0353). The BCU (0353) may further include logic controllers to control transfer of information, electric circuits to receive/transmit signals and microcontrollers to interface with the automated processes. For example, the BCU (0353) may turn on an output valve on the BSU(s) (0351) and an input value on the SEGU (0352) enabling biogas fluid transfer.

In another preferred exemplary embodiment, the BCU (0353) may be electronically coupled to an Anaerobic Digestive Units (ADUs) (0360). The ADUs (0360) may store and transfer biogas to the SEGU (0352) directly.

The utility company may communicate directly with the BCU (0353) via a manual communication link for example, a communications link to an operator delivered via a telephone call. In a preferred exemplary embodiment, a manual communication link, for example a telephone, may be used to communicate utility company on-demand requests to biogas producers.

Preferred Embodiment "Behind the Meter" Biogas Generation Unit (BGU) (0320)

Figure 3B:
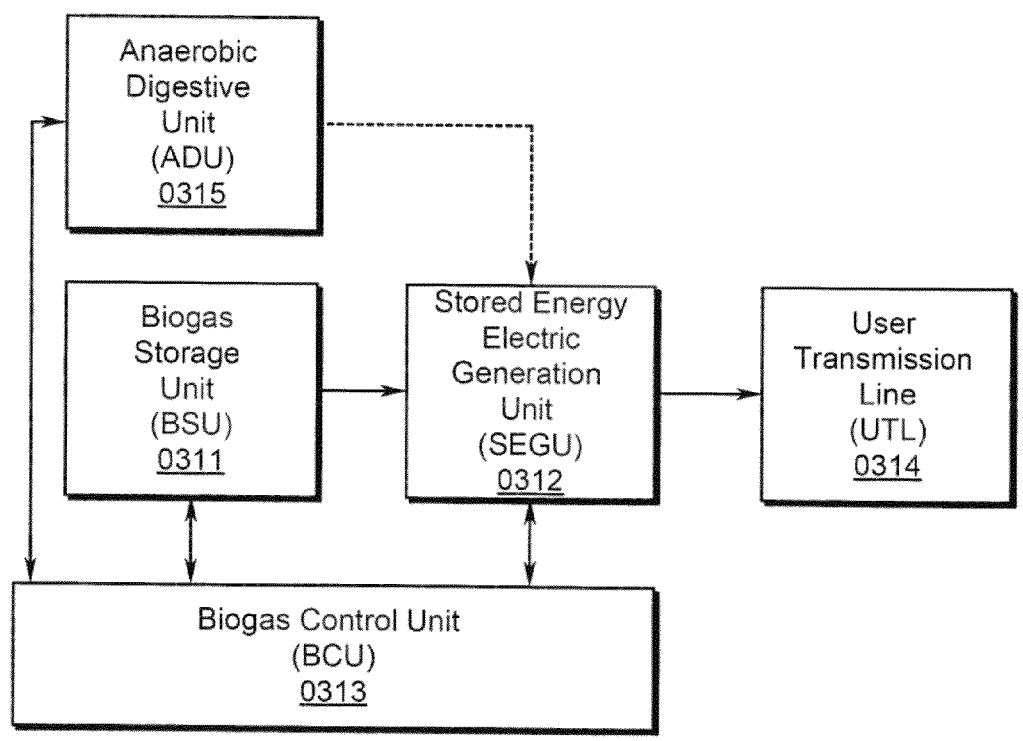
FIG. 3b illustrates an exemplary block overview of a bioenergy system supplying "behind the meter" electrical energy to users according to a presently preferred embodiment of the present invention.

The present invention may be seen in more detail as generally illustrated in FIG. 3b (0320), wherein a biogas storage unit (BSU) (0311) is in fluid communication with an stored energy electrical generation unit (SEGU) (0312). According to a preferred exemplary embodiment, plural BSUs (0311) may be in fluid communication with the SEGU (0312). An ADU (0315) may also supply biogas to SEGU (0312). According to a preferred exemplary embodiment, SEGU (0312) may generate electricity to dispatch to a user transmission line (UTL) (0314) that may supply electricity to plural user's on-demand or scheduled. This form of "behind the meter" energy supply is not controlled/dispatched by the UCU (0307), rather it is stored and used to supply power to a user (industrial user, agricultural user, small battery systems for residential users)—not set up to supply power to the grid when instructed to do so by the UCU (0307). It is "behind the meter" because it supplies the UTL (0314) not the ETG (0304). In this configuration, the BCU (0353) may be programmed to initiate energy delivery from the SEGU (0312) on a schedule such as by time of day or day of week or any other factor if BSU (0311) has biogas availability.

Preferred Embodiment Hybrid Generation Unit (HGU) (0330)

Figure 3C:
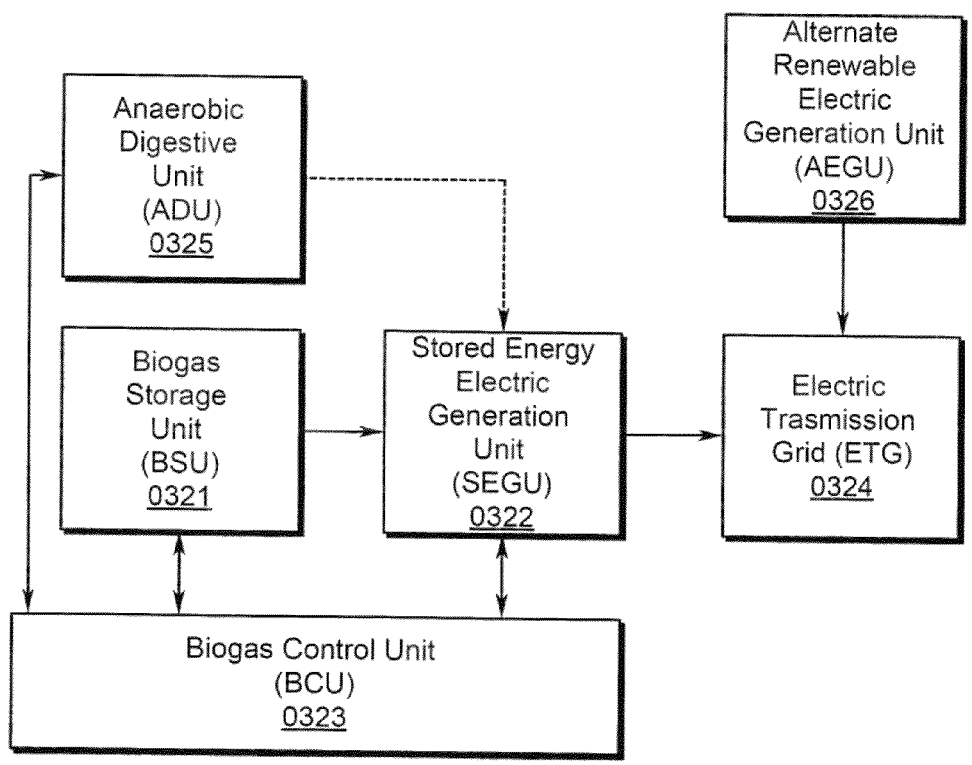
FIG. 3c illustrates an exemplary system block overview of a hybrid biogas generation system with different types of ADUs and BGUs processing different fractions or types of organic materials or other intermittent renewable energy source(s) describing a presently preferred embodiment of the present invention.

An exemplary embodiment may be seen in more detail as generally illustrated in FIG. 3c (0330), wherein a biogas storage unit (BSU) (0321) is in fluid communication with a stored energy electrical generation unit (SEGU) (0322). An alternate intermittent renewable electric generation unit (AEGU) (0326) may also be combined with SEGU (0322) to generate and supply the ETG (0324) with electricity. The intermittent sources used for AEGU (0326) may be wind turbines or solar cells.

Preferred Embodiment Automatic Communication System Block Diagram (0300)

Figure 3D:
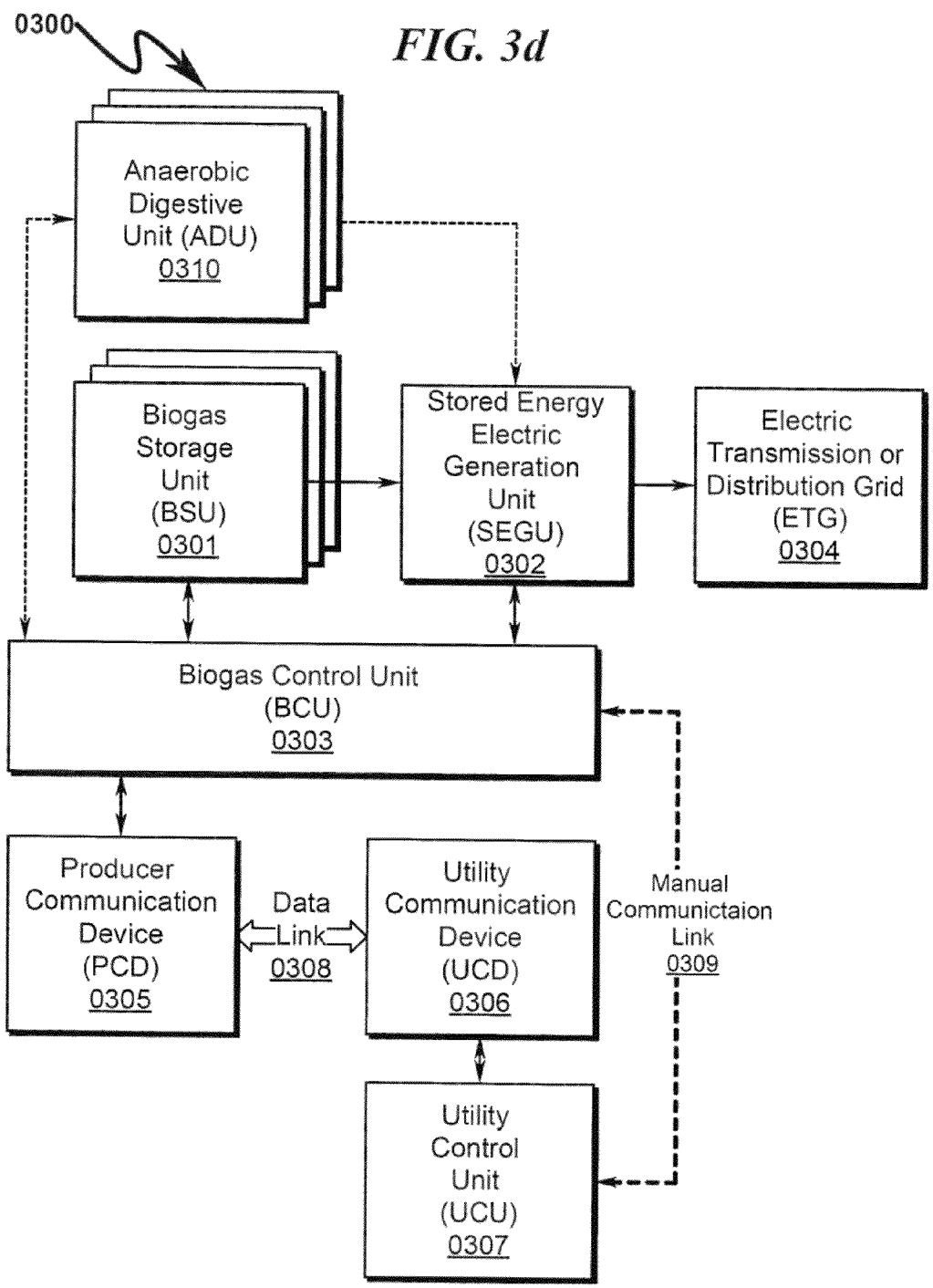
FIG. 3d illustrates an exemplary system automatic communication system overview describing a presently preferred embodiment of the present invention.

The present invention may be seen in more detail as generally illustrated in FIG. 3d (0300), wherein a biogas storage unit (BSU) (0301) is in fluid communication with a stored energy electrical generation unit (SEGU) (0302). According to a preferred exemplary embodiment, plural BSUs (0301) may be in fluid communication with the SEGU (0302).

The BSU(s) (0301) may be configured to transfer biogas to SEGU (0302) using a conduit large enough for safe and efficient transfer. The conduit may be controlled by auxiliary control systems and valves. The BSU(s) (0301) may be connected to a biogas generation unit (BGU) that further comprises operational units as described below in FIG. 4. In a preferred exemplary embodiment the BGU may be configured to connect to the SEGU (0302) directly to supply biogas. The SEGU (0302) further comprises operational units that are described below in FIG. 10. In some cases, when the BSU(s) (0301) and the SEGU (0302) are separated by long distances, a pump or blower may be used to transfer the biogas. Additionally, manual storage equipment may also be used to transport the biogas.

A biogas control unit (BCU) (0303) may be electronically connected to the BSU(s) (0301), the SEGU (0302) and a producer communication device (PCD) (0305). The BCU (0303) may use analog or digital electronic signals to control remote units and sensors. A user may invoke an automated process using a graphical user interface (GUI) on BCU (0303). FIG. 11 as generally described below, further provides additional details for BCU (0303). The BCU (0303) may further include logic controllers to control transfer of information, electric circuits to receive/transmit signals and microcontrollers to interface with the automated processes. For example, BCU (0303) may turn on an output valve on BSU(s) (0301) and an input value on SEGU (0302) enabling biogas fluid transfer.

In another preferred exemplary embodiment, the BCU (0303) may be electronically coupled to an Anaerobic Digestive Units (ADUs) (0310). The ADUs (0310) may store and transfer biogas to the SEGU (0302) directly.

The BCU (0303) is also configured to communicate electronically with PCD (0305). The PCD (0305) may be used to transmit and receive information from a utility communication device (UCD) (0306) via an established data link (0308). The PCD (0305) and UCD (0306) may be similar to intelligent communication devices (ICD) that are generally used in smart grid technology. A utility company that operates a utility control unit (UCU) (0307) may remotely control UCD (0306) and monitor its status. The utility company may also communicate with BCU (0303) directly via a manual communication link (0309) for example via a communications to an operator delivered via a telephone call. Further details of the interactions of BCU (0303), PCD (0305), UCD (0306) and UCU (0307) are described in FIG. 8. The UCU (0307) may send requests for electric power (REP) to BCU (0303) via data link (0308). Likewise, BCU (0303) may respond back to UCU (0307) via data link (0308). According to a preferred exemplary embodiment, the above described communication method may be used to meet on-demand requests for electric power from renewable sources. In another preferred exemplary embodiment, a manual communication link (0309), for example a telephone, may be used to communicate utility company on-demand requests to biogas producers.

Preferred Embodiment Biogas Generation Unit (BGU) (0400)

Figure 4:
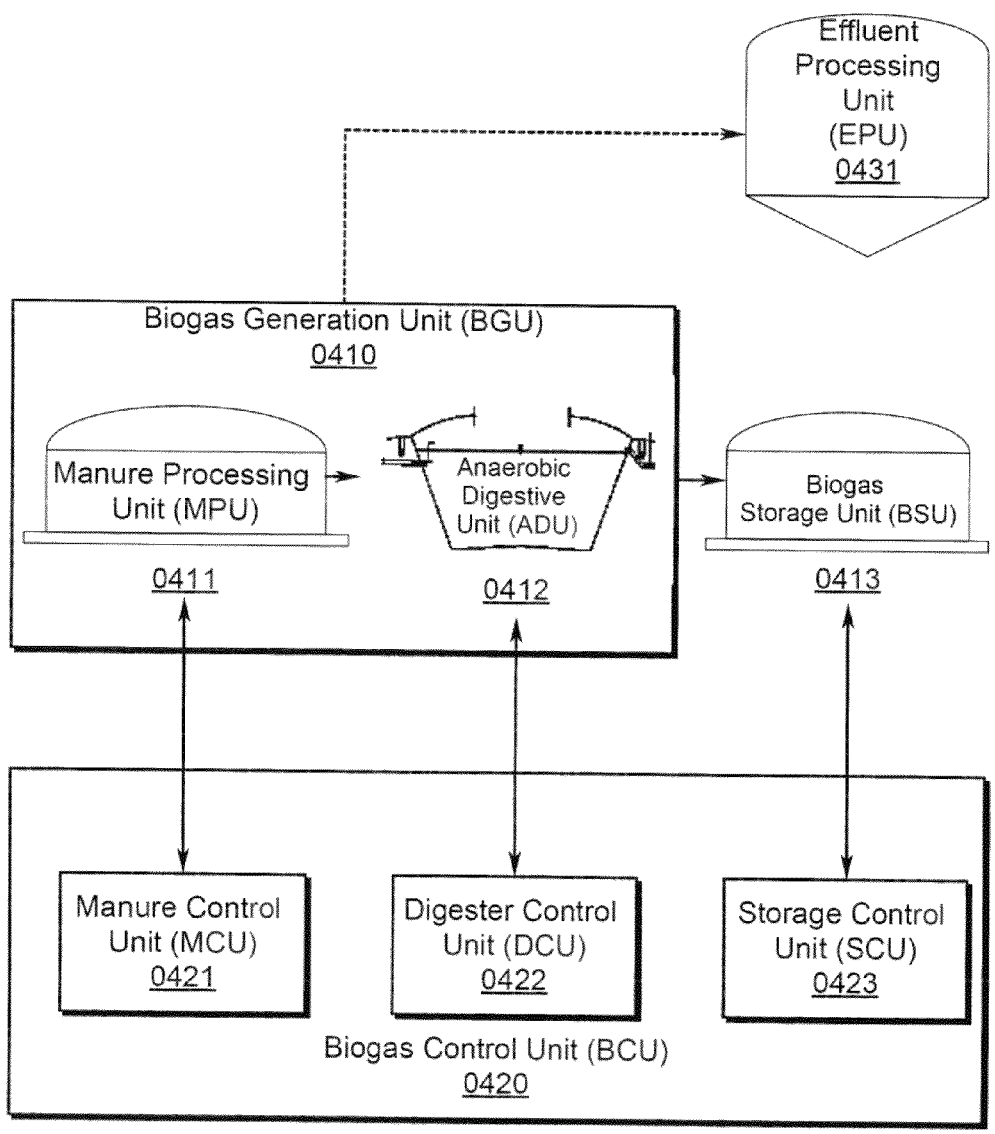
FIG. 4 illustrates an exemplary block diagram of a preferred exemplary biogas generation unit (BGU) embodiment.

The present invention may be seen in more detail as generally illustrated in FIG. 4 (0400), wherein a biogas generation unit (BGU) (0410) includes a manure processing unit (MPU) (0411) and an anaerobic digestive unit (ADU) (0412). BGU (0410) may be operatively connected to a biogas storage unit (BSU) (0413). The operation and control of MPU (0411) may be remotely managed by a manure control unit (MCU) (0421). Similarly, the operation and control of ADU (0412) may be remotely managed by a digester control unit (DCU) (0422) and the operation and control of BSU (0413) may be remotely managed by a storage control unit (SCU) (0423). A central control system (CCS) in the BCU (0420) may include MCU (0421), ADU (0422) and SCU (0423) as part of the overall control system.

According to one preferred embodiment, dairy farm manure (DFM) may be collected from one or more dairy farms in the form of liquid or solid influent and then processed in MPU (0411). The DFM collection may be integrated into existing dairy farm operation. The energy in the methane that is produced naturally by anaerobic decomposition of the DFM would otherwise be wasted and released into the atmosphere, if not collected and stored. The MPU (0411) may include a collection pit, a processing pit, flush or scrape manure collection systems and/or mechanical separators. A pump and agitation system may transfer the DFM from the pit to an inclined screen solids separator where wet fibrous solids are separated from the liquid influent. The MCU (0421) may measure flows and control and monitor the operation of MPU (0411). For example, MCU (0421) may control the transport of processed DFM from the MPU (0411) to the ADU (0412). The MPU (0411) may also be configured to separate the solids/organics from DFM before transporting to the ADU (0412). The organics could be collected from agricultural substrates, human waste being processed at a waste water plant, or organic fraction of municipal solid waste stream (OFMSW). In one preferred exemplary embodiment, the ADU (0412) may receive feedstock from a combination of the organics such as agricultural substrates, human waste from waste water plant, OFMSW or DFM. It should be noted that any of the abovementioned combinations may be used in a hybrid manner to feed ADU (0412) for biogas production.

Additionally, the MPU (0411) may further concentrate, separate or direct already separated organics and/or manure such that the high solids portion of a feedstock goes to one type of ADU configured for high solids such as a continuous stirred tank reactor ("CSTR") and/or a plug flow reactor and the low solids content portion goes to a covered lagoon ADU or a similar type ADU (0412) more suited to low solids. The MPU (0411) may incorporate a tank or in ground plug flow digester (typically operating at a mesophillic or thermophillic temperature) for processing separated solids with a high total solids content around 5 to 20% total solids operating in parallel with a lagoon style digester (typically operating at a pyschrophilic temperature, i.e., ambient) which handles the low total solids concentration liquids (typically less than 5% total solids). The hybrid arrangement may allow for an improved system to bio digester and process dilute effluents.

In one preferred exemplary embodiment, the MPU (0411) and the ADU (0412) may co-exist in one location or separated by a long distance. If the MPU (0411) and the ADU (0412) co-exist in one location, a conduit may be used to transfer processed DFM to the ADU (0412). A pump may be used to pump the DFM. A transport mechanism may be used to transfer DFM, if the MPU (0411) and the ADU (0412) are separated by long distances. Determination of using the transport mechanism or a pump to transfer DFM may be made depending on factors such as distance, volume of DFM and pumping capacity.

Anaerobic digestion process (ADP) is a series of biochemical reactions by which microorganisms break down biodegradable material such as DFM, in the absence of oxygen. In the ADU (0412), microorganisms break down the DFM and create biogas, which is then trapped in the digester. The captured biogas primarily consists of methane, a potent greenhouse gas. One of the bi-products of ADP is carbon-dioxide. An equation describing ADP biogas production is as follows:

$$C_6H_{12}O_6 \rightarrow 3CO_2 + 3CH_4$$

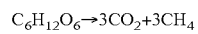

The conversion of the DFM's organic nitrogen to its inorganic form (over 60% conversion) makes the nitrogen more available to the crops.

According to a preferred exemplary embodiment, various pasteurization and concentration techniques may be used to convert the bi-products from ADP into valuable co-products including fertilizer. The bi-products may be transferred to an Effluent Processing Unit (EPU) (0431) that processes the bi-products to produce a fertilizer. The fertilizer may be marketed for use in agricultural farms.

The DCU (0422) may control the temperature of ADP and regulate input/output and other operations of ADU (0412). The DCU (0422) may further monitor the quality of biogas and the concentration of methane in the biogas using a generally available gas analyzer. The BCU (0420) may use the measured quality of biogas to calculate available electrical power (AEP) generation potential.

The BCU (0420) may use pressure sensors, laser scanning and/or optical scanning systems to measure the loft and elevation of a flexible cover base BSU (0413) and thus integrate and calculate the volume of stored biogas, stored energy value and available electric energy production or available electric power (AEP).

The ADU (0412) may be configured to transfer biogas to BSU (0413) using a conduit large enough for safe and efficient transfer. The ADU (0412) may also be used to store and transfer biogas to SEGU. Auxiliary control systems and valves in BCU (0420) may remotely control operations of the conduit.

Selection of an appropriate biogas storage system may make a significant contribution to the efficiency and safety of a bioenergy system. A biogas storage system may also compensate for fluctuations in the production and consumption of biogas as well as temperature-related changes in volume. The BSU (0413) may be a bioenergy storage system that typically operates at pressures below 2 psi. The BSU (0413) may be made of steel, fiberglass, or a flexible fabric. A separate tank may be used with a floating gas holder for the storage of the digestate (bi-product) and also storage of the raw biogas.

In a preferred exemplary embodiment the BSU (0413) and the ADU (0412) are integrated into a single system such as a covered lagoon digester with a flexible covering that may have folds built into it or be sufficiently flexible to able to expand and store the produced biogas and still sustain and maintain its integrity under worst case wind loads.

The BSU (0413) may also be a gas holder with a flexible inflatable fabric top. Flexible membrane materials commonly used for these gas holders may include high-density polyethylene (HDPE), low-density polyethylene (LDPE), linear low density polyethylene (LLDPE), and chlorosulfonated polyethylene covered polyester. Thicknesses for cover materials typically may vary from 0.5 to 2.5 millimeters. According to a preferred exemplary embodiment, BSU (0413) may store biogas for a period of less than 7 days.

According to one preferred exemplary embodiment, ADU (0412) may act as a self-contained biogas storage unit. After completing ADP process, ADU (0412) may produce and store the biogas in ADU (0412) and directly transfers the biogas gas to SEGU (0302), when instructed by BCU (0420). The ADU (0412) may include a flexible membrane inflatable top that expands as needed to allow for more biogas storage. Materials used for the inflatable top may be similar to the materials used in BSU (0413) as described above. Depending on the capacity and demand of biogas, ADU (0412) may store biogas independently or in conjunction with a BSU (0413).

According to another preferred exemplary embodiment, plural ADUs (0412) may produce, store, and transfer biogas to SEGU (0302) for generating electrical power. The ADU's (0412) may store the biogas for less than 7 days.

According to yet another preferred exemplary embodiment, plural ADUs may store and transfer biogas to plural BSUs or a standalone BSU.

Preferred Exemplary Method Embodiment (0520)

As generally seen in the flow chart of FIG. 5 (0520), the present invention method may be generally described in terms of the following steps:

(1) with the BCU, waiting for a request for electrical power (REP) indicating quantity (power level and duration) from a utility company (0521);
(2) with the BCU, acknowledging the REP to the utility company (0522);
(1) with the BCU, calculating available electrical energy and power (AEP) from the stored biogas (0523); BCU ensures the contracted amount of stored energy is available example 10 MWhrs if this is the contract mechanism;
(3) with the BCU, determining if the AEP is greater than 0, and if so, proceeding to step (0527) (0524);
(4) with the BCU, responding with non-availability to the utility company (0525);
(5) with the BGU, generating biogas and proceeding to the step (0521) (0526);
(6) with the BCU, responding with the AEP quantity to the utility company (0527);
(7) with the utility company, sending authorization to the BCU, for a negotiated electrical power (NEP) that is less than or equal to the AEP (0528);
(8) with the BCU, determining if the NEP is required instantaneously, and if not, proceeding to step (0531) (0529);
(9) with the BCU, connecting the SEGU to the ETG, transmitting the NEP and proceeding to the step (0521) (0530); and
(10) with the BCU, connecting the SEGU to the ETG at a scheduled time, transmitting the NEP and proceeding to the step (0521) (0531).

One skilled in the art will recognize that these method steps may be augmented or rearranged without limiting the teachings of the present invention. This general method summary may be augmented by the various elements described herein to produce a wide variety of invention embodiments consistent with this overall design description.

Preferred Exemplary Biogas Storage Automatic Communication Method Embodiment (0500)

As generally seen in the Biogas Storage Automatic Communication flow chart of FIG. 5a (0500), the present invention method may be generally described in terms of the following steps:

(1) with the PCD, establishing a network connection with the UCD (0501);
(2) with the BCU, waiting for a request for electrical power (REP) from the UCD (0502);
(3) with the PCD, receiving the REP indicating quantity (power level and duration) from the UCU via the UCD (0503);
(4) with the PCD, acknowledging the REP to the UCD and forwarding the REP to the BCU (0504);
(2) with the BCU, calculating available electrical energy and power (AEP) from the stored biogas (0505); BCU ensures the contracted amount of stored energy is available example 10 MWhrs if this is the contract mechanism;
(5) with the BCU, determining if the AEP is greater than 0, and if so, proceeding to step (0508) (0506);
(6) with the BCU, responding with non-availability of the REP to the UCU via the PCD and the UCD (0507);
(7) with the BGU, generating biogas and proceeding to the step (0502) (0508);
(8) with the BCU, responding with the AEP quantity to the UCU via the PCD and the UCD (0509);

(9) with the UCU, sending authorization to the BCU via the UCD and the PCD, for a negotiated electrical power (NEP) that is less than or equal to the AEP (0510);

(10) with the BCU, determining if the NEP is required instantaneously, and if not, proceeding to step (0513) (0511);

(11) with the BCU, connecting the SEGU to the ETG, transmitting the NEP and proceeding to the step (0502) (0512); and

(12) with the BCU, connecting the SEGU to the ETG at a scheduled time, transmitting the NEP and proceeding to the step (0502) (0513).

One skilled in the art will recognize that these method steps may be augmented or rearranged without limiting the teachings of the present invention. This general method summary may be augmented by the various elements described herein to produce a wide variety of invention embodiments consistent with this overall design description.

Preferred Exemplary Available Electric Power (AEP) Determination Method Embodiment (0600)

Figure 6:
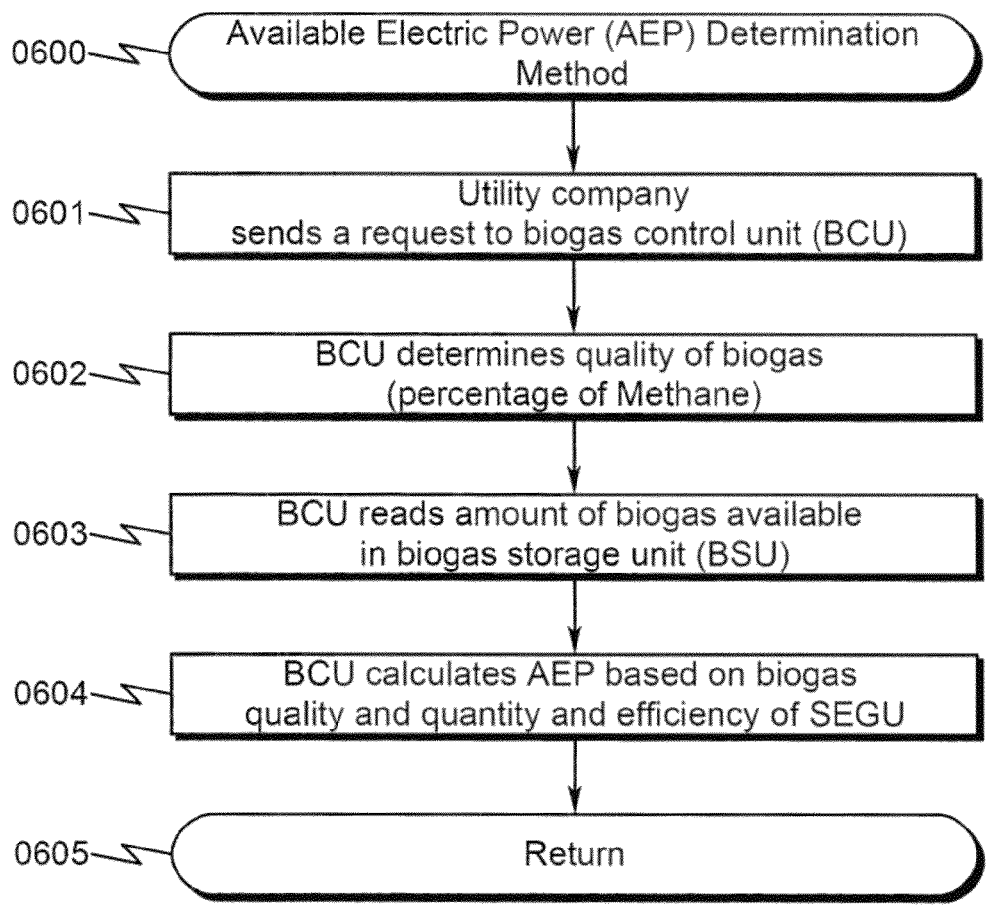
FIG. 6 illustrates a detailed flowchart of a preferred exemplary available electrical power (AEP) calculation method used in some preferred exemplary invention embodiments.

As generally seen in the flow chart of FIG. 6 (0600), a preferred exemplary available electric power (AEP) determination method may be generally described in terms of the following steps:

(1) with the utility company, forwarding a request to BCU for determining AEP (0601);

(2) with the BCU, determining quality of biogas by measuring the percentage of methane in the BSU (0602);

(3) with the BCU, determining quantity of biogas by measuring the percentage of methane in the BSU (0603);

(4) with the BCU, calculating AEP based on the quality and the quantity of biogas available in the BSU and the efficiency of EGU (0604); and (5) Returning to the step (0504) (0605).

AEP may be calculated as a function of gas volume in the BSU/ADP, methane percentage, pressure, temperature, and calorific value of methane. Gas volume may be calculated as a function of storage vessel dimensions, level of inflation or expansion of the BSU/ADP.

Gas volume for a flexible inflatable covered BSU/ADP may be determined by measuring the height of inflation and/or more accurately by scanning the inflated cover with a laser or optical or other type of remote scanning device and integrating the results. A laser scanner as used by surveyors to calculate the volume of a pile could continuously scan and monitor the cover height and shape of a BSU using a flexible cover. A software algorithm ("fuel gauge") may calculate AEP based on the calculated volume, pressure, methane percentage and other factors. This "fuel gauge" could be used to guarantee contracted obligations to show sufficient stored energy availability and recharge rates after a discharge.

Preferred Exemplary Biogas Production and Control Method Embodiment (0700)

Figure 7:
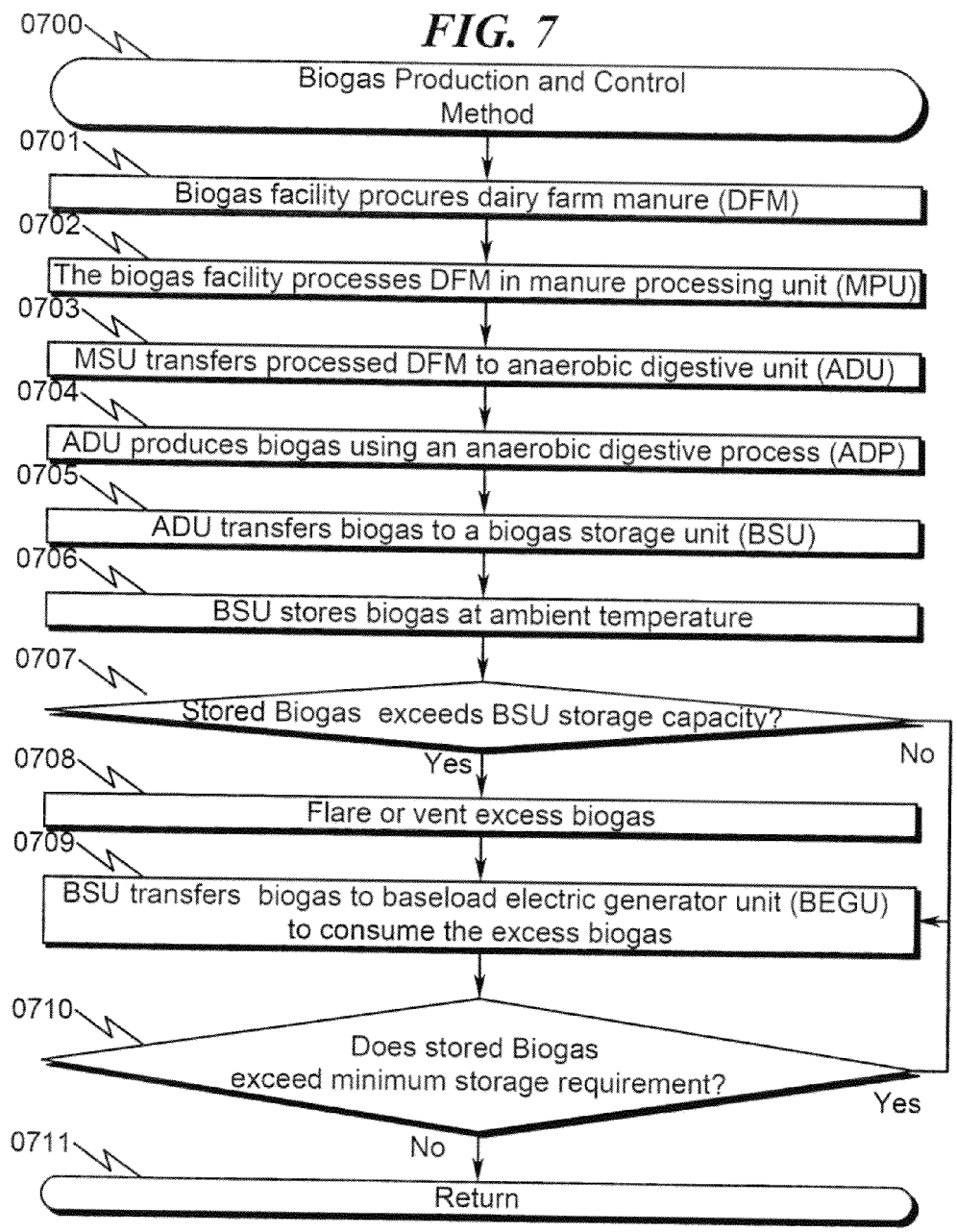
FIG. 7 illustrates a detailed flowchart of a preferred exemplary biogas generation and control method used in some preferred exemplary invention embodiments.

As generally seen in the flow chart of FIG. 7 (0700), a preferred exemplary biogas production and control method may be generally described in terms of the following steps:

(1) with biogas facility, procuring dairy farm manure (DFM) (0701);

(2) with the MPU, processing the procured DFM to extract solids from the DFM (0702);

(3) with the MPU, transferring the processed DFM to the ADU (0703);

(4) with the ADU, producing biogas through ADP (0704);

(5) with the ADU, transferring the biogas to the BSU (0705);

(6) with the BSU, storing the biogas in the BSU at ambient temperature (0706);

(7) with the BCU, determining if stored biogas exceeds the capacity of the BSU, if not, proceeding to step (0710) (0707);

(8) with an excess biogas processing unit (EPU), flaring or venting the excess biogas (0708);

(9) with the BSU, transferring the biogas to a base load electric generation unit BEGU (0709);

(10) with the BCU, determining if the remaining stored biogas exceeds minimum biogas storage requirements to meet contractual biogas energy demand (for example, biogas required to generate electricity for 4 hours a day), if so, proceeding to step (0709) (0710) ; and

(11) returning to step (0507) (0711).

Preferred Embodiment Control and Communication System (0800)

Figure 8:
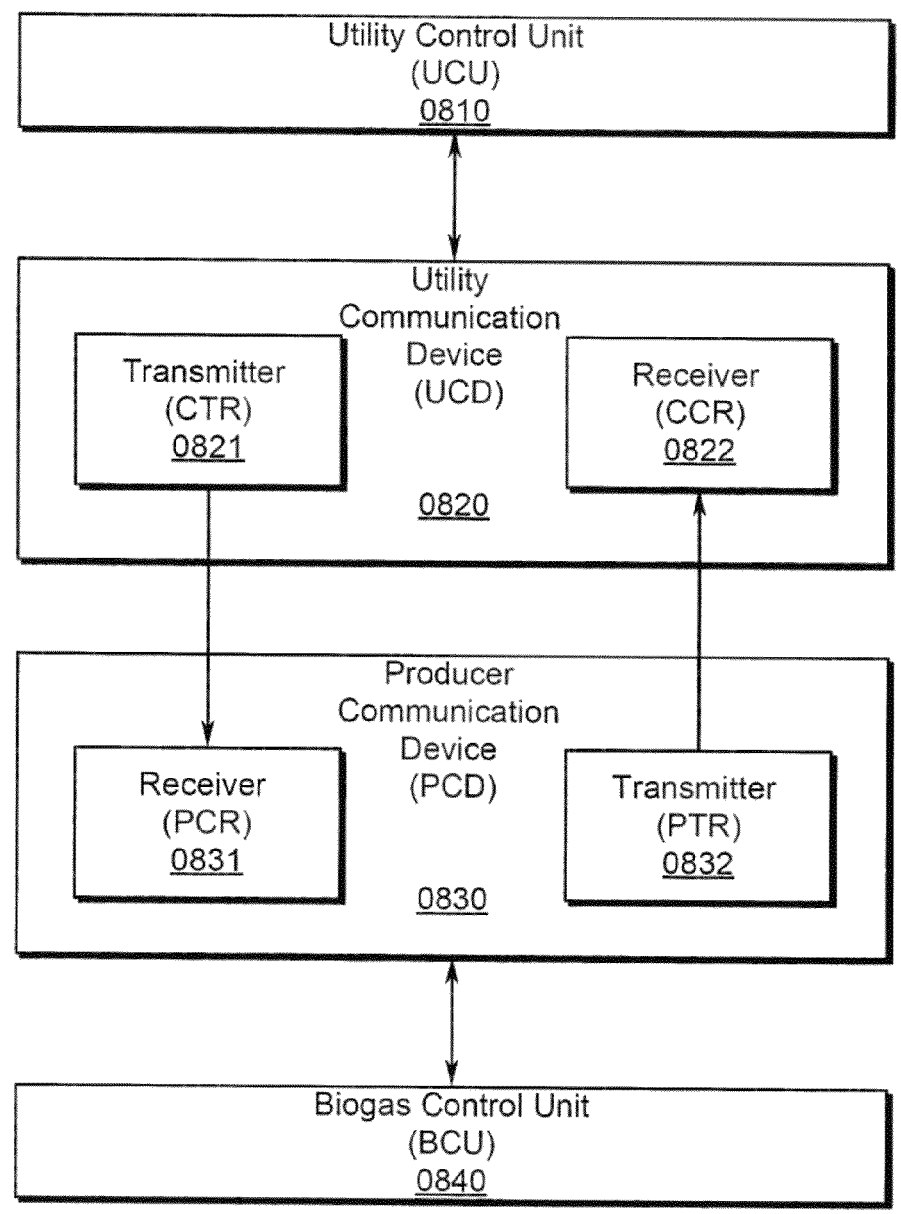
FIG. 8 illustrates an exemplary block diagram of a preferred exemplary control and communication system.

The present invention may be seen in more detail as generally illustrated in FIG. 8 (0800), wherein a control and communication system is described. The system may include a utility control unit (UCU) (0810), a utility communication device (UCD) (0820), a producer communication device (PCD) (0830), and a biogas control unit (BCU) (0840).

An electric utility company (EUC) may manage the operation and control of UCU (0810). The EUC may have a central control system that manages energy suppliers such as renewable energy producers and may manage and monitor consumers such as residential and industrial customers via smart meters. The EUC may also calculate and forecast demand based on consumer needs and history. Additionally, EUC may need to meet the demand with a supply from the producers. Furthermore, the EUC may instruct UCU (0810) to generate a request for electrical power (REP) based on the demand. In some instances, EUC may not be able to accurately forecast demand and might need immediate or instantaneous supply of electric power, for example in 10 minutes. In these cases, EUC may instruct UCU (0810) to generate a request indicating the instantaneous nature of the request. The UCU (0810) may be connected to UCD (0820) and also configured to send and receive requests to UCD (0820).

In a preferred exemplary embodiment, if the need for electrical power is instantaneous, an electrochemical battery of relatively short duration (capacity) may be placed between the SEGU and the utility with sufficient power and duration to instantaneously provide power and energy thus bridging the time the SEGU needs to power up and come on line which typically may be within a few minutes.

The UCD (0820) is a communication device that may include a transmitter (CTR) (0821) and a receiver (CCR) (0822). Likewise, PCD (0830) is a communication device that may include a transmitter (PTR) (0832) and a receiver (PCR) (0831). The CTR (0821) may be connected to PCR (0831) for transmitting data such as request for electric power (REP). Similarly, CCR (0822) may be connected to PTR (0832) for receiving data such as responses for REP.

A network connection may need to be established between UCD (0820) and PCD (0830) before communicating with each other. The network connection may be a wired connection using a copper wire or a wireless connection using such protocols as 3G, 4G, or LTE. The wired connection may be established by a generally available protocol such as Ethernet. Once a network connection is established between UCD (0820) and PCD (0830), UCU (0810) may send a REP and receive a response from BCU (0840).

The BCU (0840) may be connected to PCD (0830) and also configured to send and receive requests to PCD (0830).

According to a preferred exemplary embodiment, UCU (0810) may generate REP instantaneously or schedule REP for a later time. The CTR (0821) may transmit the REP to PCR (0831). The PCR (0831) may parse the request and forward it to BCU (0840). The BCU (0840) may then process the REP and send a response back to PCD (0830) indicating available electric power (AEP). The PTR (0832) may send the response to CCR (0822) which may then forward to UCU (0810) for further processing.

According to a preferred exemplary embodiment, the communication channel from UCU (0810) to BCU (0840) may be kept open at all times to fulfill on-demand energy requirements round-the-clock.

Preferred Exemplary Communication Flowchart Embodiment (0900)

Figure 9:
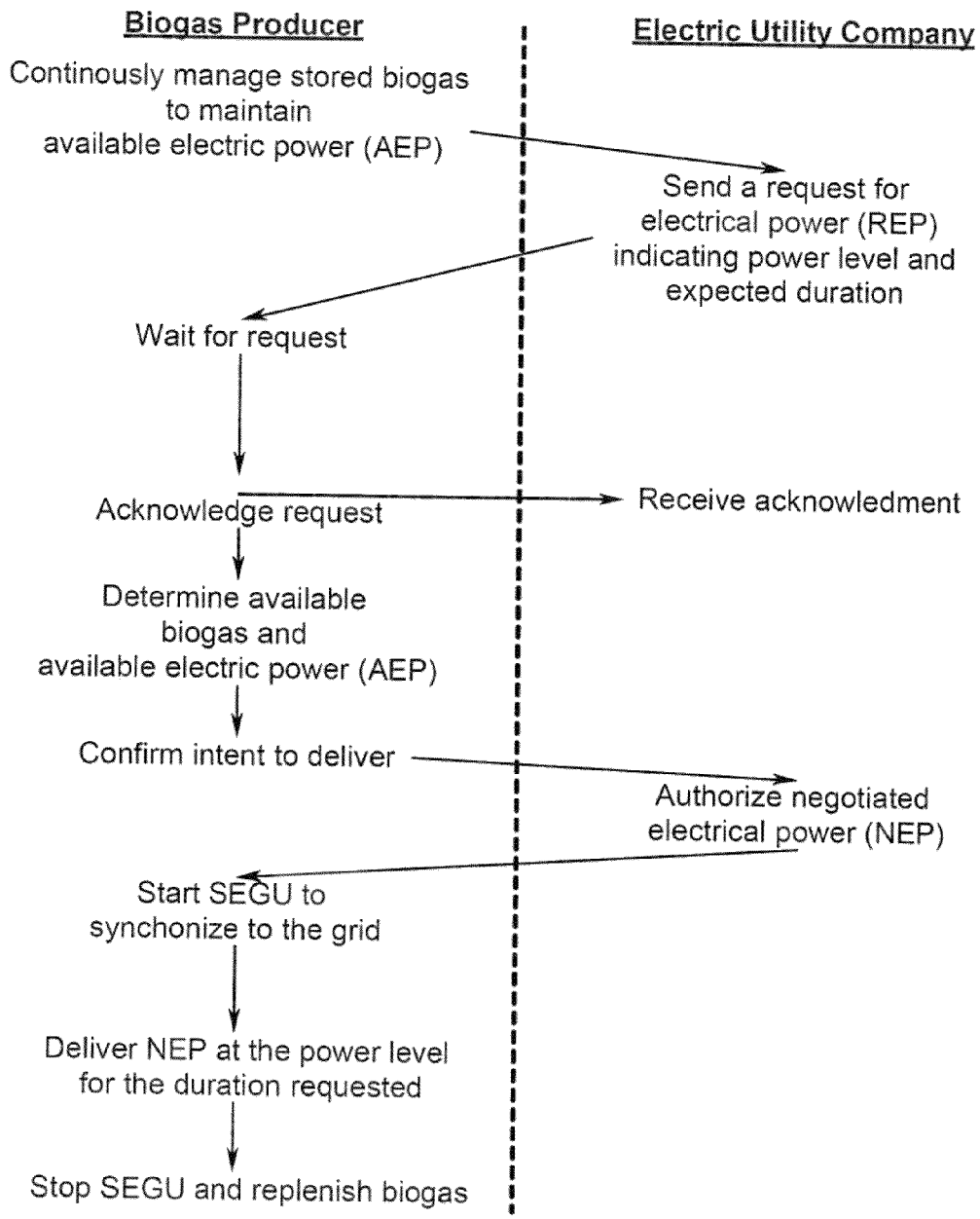
FIG. 9 illustrates a flowchart of a preferred exemplary communication method used in some preferred exemplary invention embodiments.

As generally seen in the flow chart of FIG. 9 (0900), a preferred exemplary bioenergy system communication flowchart may include a BCU (0303) continuously managing stored biogas to maintain available electrical power (AEP). The UCU (0307) may initiate a request for electric power (REP) indicating quantity required (power level and duration). The UCU (0307) may communicate directly with BCU (0303) via a manual communication link (0309), for example a telephone call or a hotline. A network connection (data link (0308)) between UCD (0306) and PCD (0305) may be established. The network connection may be wired or wireless. The REP may be forwarded to UCD (0306) which subsequently transmits the REP to PCD (0305). The PCD (0305) forwards the request to BCU (0303) for further processing. The BCU (0303), which is waiting for a REP, acknowledges the request to UCU (0303) via data link (0308).

The BCU (0303) may then parse the received REP and extract quantity required. The BCU (0303) may calculate available electrical power (AEP) based on quality and quantity of stored biogas in BGU (0301) and efficiency of SEGU (0302). The AEP may be less than or more than the REP. The BCU (0303) may acknowledge with AEP quantity. In some cases, a price may be pre-negotiated in an existing contract between the EUC and the bioenergy producer. The acknowledgement is forwarded to UCU (0307) via data link (0308).

The UCU (0307) may send an authorization back to BCU (0303) with a negotiated electrical power quantity (NEP). The UCU (0307) may also indicate in the authorization, if the NEP is required instantaneously or scheduled for a later time. The BCU (0303) may receive the authorization and determine the urgency of transmitting NEP. If NEP is instantaneously required, BCU (0303) may remotely send a signal to start a generator in SEGU (0302) and synchronize to the ETG (0304). Otherwise, BCU (0303) may schedule the coupling for the requested schedule time. The BCU (0303) may stop BEGU to replenish biogas and start BEGU when a required minimum biogas is stored.

Preferred Embodiment Electrical Generation Unit (EGU) (1000)

Figure 10:
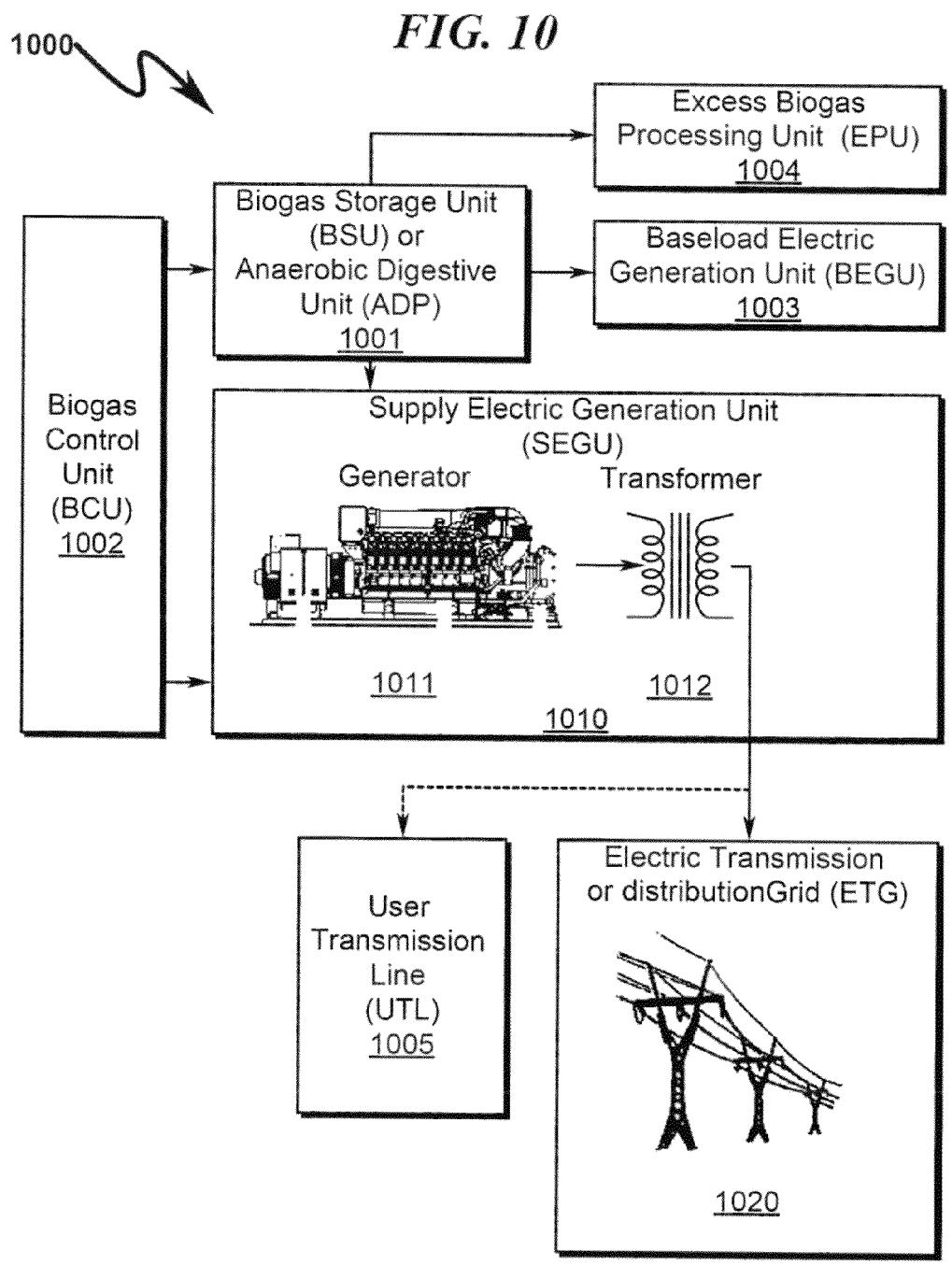
FIG. 10 illustrates an exemplary block diagram of a preferred exemplary electrical generation unit (EGU) embodiment.

The present invention may be seen in more detail as generally illustrated in FIG. 10 (1000), wherein a biogas storage unit (BSU) and/or anaerobic digestive unit (ADP) (1001) are configured to transfer gas to a stored energy electric generation unit (SEGU) (1010), a base load electric generation unit (BEGU) (1003) and a excess biogas processing unit (EPU) (1004). The SEGU (1010) is configured to be controlled electronically by BCU (1002). Upon receiving a control signal from BCU (1002), SEGU (1010) may electrically couple to ETG (1020) transmitting electrical power over ETG (1020).

The BEGU (1003) may operate continuously to consume excess biogas generated from the BSU/ADP (1001). The BEGU (1003) may run under a load or no load. The EPU (1004) may be used to flare or vent excess biogas. A combination of EPU (1004) and BEGU (1003) may be used to consume or burn excess biogas. The BCU (1002) monitors stored biogas in BSU (1001) to ensure minimum required biogas volume is present in order to meet contractual conditions. For example, the contract might include delivering electrical power for 4 hours during a certain time of each day. In the remaining part of the day, excess biogas produced is flared or vented in EPU (1004) or consumed in BEGU (1003).

The SEGU (1010) may further comprise an electric generator (1011) coupled to an electric transformer (1012). The generator (1011) receives biogas from BSU/ADP (1001) and converts it into electrical power using a combustion process. Typically, generator (1011) uses the energy in the biogas to drive a crank shaft. The crank shaft turns an alternator to produce electricity. Heat is also produced during this process. The efficiency of the generator may be taken into account when the electrical output is calculated.

The output from the generator (1011) may be transformed into the required voltage and frequency that conforms to ETG (1020). The transformer (1012) with a circuit breaker may be used to synchronize the frequency (example 50 Hz) of the generated electrical power to the ETG (1020).

According to a preferred exemplary embodiment, the generator (1011) may use a spinning reserve of biogas to keep running in idle without a load. For example, generator (1011) may rotate at a constant 1500 revolutions per minute in idle mode. This enables the generator to instantaneously generate electrical power without delay, when a request for instantaneous power is received. Business factors may enable bioenergy producers to negotiate a better price that would offset the spinning reserve biogas used for running generator (1011) in idle mode. Additionally, bioenergy producers may negotiate pricing schedule with EUCs based on time of the day and urgency of the request. This would allow for bioenergy producers to have a profitable business model.

According to a further preferred exemplary embodiment, the BEGU (1003) and the SEGU (1010) may be combined as one electric generation unit (EGU) but partitioned or segmented. The BCU (1002) may instruct the utilization percentages of BEGU (1003) and SEGU (1010). For example BCU may instruct to combine 50 percent BEGU (1003) and 50 percent SEGU (1010) to generate electricity to the ETG (1020).

According to yet another preferred exemplary embodiment, the SEGU (1010) may be coupled directly to a user transmission line (UTL) (1005) to provide on-demand "behind the meter" electricity.

Preferred Embodiment Biogas Control Unit (BCU) (1100)

The present invention may be seen in more detail as generally illustrated in FIG. 11 (1100), wherein BCU (1101) includes a biogas computing device (BCD) (1110) that is configured for enabling users such as process control engineers, operators, managers to interact with central control system (CCS) (1105). The BCU (1101) may further comprise a logic controller (1103) that directs data flow, a CCS (1105), a network controller (1104) that enables remote network connection, a microcontroller (1102) that executes instructions read from a computer-readable medium (1111), and a graphical user interface (GUI) (1112) with a pointing device. The CCS (1105) may further comprise control units such as MCU, DCU, and SCU that control MPU, ADU and BSU respectively. The users may login to BCU (1101) directly or remotely through a network connection. After logging in, users may open GUI (1112) with the pointing device and launch CCS (1105) module to monitor/control various components of the bioenergy system. Additionally, users may use GUI (1112) to invoke processes that automatically wait for a request for electrical power (REP) and subsequently process received requests from UCUs. The BCU (1101) may also calculate available electrical power (AEP) using monitored/measured data from CCS (1105) and EGU efficiency. When BCU (1101) receives authorization for electric power, CCS (1105) may automatically connect EGU to ETG transmitting on-demand power after negotiating quantity. According to the present preferred exemplary embodiment, automated processes invoked within BCU (1101) may enable efficient communication between suppliers and renewable energy producers. Furthermore, the automated processes within BCU (1101) may allow for reliable on-demand supply of dairy farm bioenergy.

System Summary

The present invention system anticipates a wide variety of variations in the basic theme of stored renewable energy utilizing stored bioenergy or biogas, but can be generalized as a bioenergy storage and management system comprising one or more of the following but not necessarily requiring all:
- (a) biogas generation unit (BGU);
- (b) biogas storage unit (BSU);
- (c) stored energy electric generation unit (SEGU); and
- (d) biogas control unit (BCU);

wherein the BGU is configured to produce biogas;
the BGU is configured to transfer the biogas to the BSU;
the BSU is configured to store the biogas;
the BSU is configured to transfer the biogas to the SEGU;
the SEGU is configured to generate electric power with the transferred biogas;
the BCU is configured to monitor the status of the BGU and the BSU;
the BCU is configured to control the operation of the BGU and the BSU;
the BCU is configured to control electrical coupling of the SEGU to an electric transmission grid (ETG); and
the BCU is configured to communicate with an utility company.

This general system summary may be augmented by the various elements described herein to produce a wide variety of invention embodiments consistent with this overall design description.

Method Summary

The present invention method anticipates a wide variety of variations in the basic theme of implementation, but can be generalized as a bioenergy storage and management method wherein the method is performed on a bioenergy storage and management system comprising:
- (a) biogas generation unit (BGU);
- (b) biogas storage unit (BSU);
- (c) stored energy electric generation unit (SEGU); and
- (d) biogas control unit (BCU);

wherein the BGU is configured to produce biogas;
the BGU is configured to transfer the biogas to the BSU;
the BSU is configured to store the biogas;
the BSU is configured to transfer the biogas to the SEGU;
the SEGU is configured to generate electric power with the transferred biogas;
the BCU is configured to monitor the status of the BGU and the BSU;
the BCU is configured to control the operation of the BGU and the BSU;
the BCU is configured to control electrical coupling of the SEGU to an electric transmission grid (ETG); and
the BCU is configured to communicate with an utility company;

wherein the method comprises the steps of:
- (1) with the BCU, waiting for a request for electrical power (REP) indicating quantity (power level and duration) from a utility company;
- (2) with the BCU, acknowledging the REP to the utility company;
- (3) with the BCU, calculating available electrical energy and power (AEP) from the stored biogas;
- (4) with the BCU, determining if the AEP is greater than 0, and if so, proceeding to step (7);
- (5) with the BCU, responding with non-availability to the utility company;
- (6) with the BGU, generating biogas and proceeding to the step (1);
- (7) with the BCU, responding with the AEP quantity to the utility company;
- (8) with the utility company, sending authorization to the BCU, for a negotiated electrical power (NEP) that is less than or equal to the AEP;
- (9) with the BCU, determining if the NEP is required instantaneously, and if not, proceeding to step (11);
- (10) with the BCU, connecting the SEGU to the ETG, transmitting the NEP and proceeding to the step (1); and
- (11) with the BCU, connecting the SEGU to the ETG at a scheduled time, transmitting the NEP and proceeding to the step (1).

This general method summary may be augmented by the various elements described herein to produce a wide variety of invention embodiments consistent with this overall design description.

System/Method Variations

The present invention anticipates a wide variety of variations in the basic theme of bioenergy. The examples presented previously do not represent the entire scope of possible usages. They are meant to cite a few of the almost limitless possibilities.

This basic system and method may be augmented with a variety of ancillary embodiments, including but not limited to:
An embodiment wherein the BGU further comprises:
    manure processing unit (MPU); and
    anaerobic digester unit (ADU);
    wherein
    the MPU is configured to process manure or organic feedstock;
    the MPU is configured to supply the processed manure or organics to the ADU;

the ADU is configured to produce the biogas using the ADP;

the ADU is configured to produce an effluent using the ADP; and the ADU is configured to transfer the biogas to the BSU.

An embodiment wherein said communication further comprises:
(a) producer communication device (PCD);
(b) utility communication device (UCD); and
(c) utility control unit (UCU);
wherein
the PCD is configured to permit remote control and monitoring of the BCU;
the PCD is configured to communicate with the UCD;
the UCD is configured to communicate with the PCD under control of the UCU; and
the UCU is configured to permit remote control and monitoring of the BCU via data transferred to and from the PCD.

An embodiment wherein:
the PCD comprises a transmitter (PTR) and a receiver (PCR);
the UCD comprises a transmitter (CTR) and a receiver (CCR);
the PTR is configured to communicate with the CCR; and
the CTR is configured to communicate with the PCR.

An embodiment wherein the SEGU further comprises:
electric generator to convert the biogas into the electrical power; and
transformer configured to electrically couple output from the electric generator to the ETG.

An embodiment wherein the SEGU further comprises:
electric generator to convert the biogas into the electrical power; and
transformer configured to electrically couple output from the electric generator to a user transmission line (UTL).

An embodiment wherein the ETG is configured to be coupled to the SEGU and an alternate renewable generation unit (AEGU).

An embodiment wherein the MPU is further configured to separate the processed manure into high content solids and low content solids.

An embodiment wherein the manure is procured from a dairy farm.

An embodiment wherein the manure is human waste procured from a waste water treatment plant.

An embodiment wherein the manure is an organic waste.

An embodiment wherein the ADU is further configured to transfer the biogas to the SEGU.

An embodiment wherein the BSU is configured to store the biogas for less than 7 days.

An embodiment wherein plural BSUs are configured to store the biogas.

An embodiment wherein the plural BSUs are configured to transfer the biogas to the SEGU.

An embodiment wherein the plural BSUs are configured to store the biogas for less than 7 days.

An embodiment wherein the ADU is further configured to store the biogas.

An embodiment wherein the ADU is configured to store the biogas for less than 7 days.

An embodiment wherein plural ADUs are configured to produce the biogas.

An embodiment wherein the plural ADUs are configured to store the biogas.

An embodiment wherein the plural ADUs are configured to transfer the biogas to the SEGU.

An embodiment wherein the plural ADUs are configured to store the biogas for less than 7 days.

An embodiment wherein the ADU is further configured to transfer the effluent to an effluent processing unit (EPU) to produce a fertilizer.

An embodiment wherein the BCU is configured to instantaneously couple the SEGU to the ETG.

An embodiment wherein the BCU is configured to schedule coupling of the SEGU to the ETG.

An embodiment wherein the PCD and the UCD are configured to communicate wirelessly.

An embodiment wherein the PCD and the UCD are configured to communicate using a wired connection.

An embodiment wherein the BCU and the UCU are configured to communicate using a manual connection.

An embodiment wherein the BCU is configured to calculate available electrical power (AEP) based on measured quality and quantity of the stored biogas in the BSU, and efficiency of the SEGU.

One skilled in the art will recognize that other embodiments are possible based on combinations of elements taught within the above invention description.

CONCLUSION

A bioenergy management system and method for generating and supplying on-demand auxiliary electrical power has been disclosed. The system/method includes a biogas generation unit (BGU) that produces biogas from digestible organic material including dairy farm manure and stores the generated biogas in a biogas storage unit (BSU). A stored energy electric generation unit (SEGU) converts the stored biogas to electricity. A biogas control unit (BCU) measures the quality and quantity of biogas stored in the BSU and calculates available electric power (AEP) from this information. Depending on auxiliary electrical power requirements, a utility control unit (UCU) initiates an on-demand request for electric power (REP) to the BCU using a producer communication device (PCD)/utility communication device (UCD) data link. The BCU processes the REP from the UCU and negotiates electrical power (NEP) quantity. The BCU may electrically connect the SEGU to an electric transmission grid (ETG) to allow instantaneous or scheduled NEP delivery to the ETG.

What is claimed is:

1. A bioenergy storage and management system comprising:
(a) biogas generation unit (BGU);
(b) biogas storage unit (BSU);
(c) stored energy electric generation unit (SEGU); and
(d) biogas control unit (BCU);
wherein
said BGU is configured to produce biogas;
said BGU is configured to transfer said biogas to said BSU;
said BSU is configured to store an amount of said biogas needed for peak demand;
said BSU is configured to transfer said biogas to said SEGU;
said SEGU is configured to generate electric power with said transferred biogas;
said BCU is configured to monitor the status of said BGU and said BSU;
said BCU is configured to control the operation of said BGU and said BSU;
said BCU is configured to control electrical coupling of said SEGU to an electric transmission grid (ETG); and said BCU is configured to initiate said SEGU in response to a remote request for on demand power from an utility company, an independent system operator, a utility intermediary entity, from an energy storage device, or from an onsite consumer.

2. The bioenergy storage and management system of claim 1 wherein said BGU further comprises:
(a) manure processing unit (MPU); and
(b) anaerobic digester unit (ADU);
wherein
said MPU is configured to process manure;
said MPU is configured to supply said processed manure to said ADU;
said ADU is configured to produce said biogas using saran Anaerobic Digestion Process (ADP);
said ADU is configured to produce an effluent using said ADP; and
said ADU is configured to transfer said biogas to said BSU.

3. The bioenergy storage and management system of claim 2 wherein said MPU is further configured to separate said processed manure into high content solids and low content solids.

4. The bioenergy storage and management system of claim 2 wherein said manure is procured from a dairy farm.

5. The bioenergy storage and management system of claim 2 wherein said ADU is further configured to transfer said biogas to said SEGU.

6. The bioenergy storage and management system of claim 2 wherein said ADU is further configured to store said biogas.

7. The bioenergy storage and management system of claim 2 wherein said ADU is further configured to transfer said effluent to an effluent processing unit (EPU) to produce a fertilizer.

8. The bioenergy storage and management system of claim 2 wherein the ADU transforms an influent into an enhanced fertilizer.

9. The bioenergy storage and management system of claim 2 wherein the ADU is configured as a lagoon digester comprising a polymer liner and an inflatable or expandable cover.

10. The bioenergy storage and management system of claim 1 wherein said communication further comprises:
(a) producer communication device (PCD);
(b) utility communication device (UCD); and
(c) utility control unit (UCU);
wherein
said PCD is configured to permit remote control and monitoring of said BCU;
said PCD is configured to communicate with said UCD;
said UCD is configured to communicate with said PCD under control of said UCU; and
said UCU is configured to permit remote control and monitoring of said BCU via data transferred to and from said PCD.

11. The bioenergy storage and management system of claim 10 wherein:
said PCD comprises a transmitter (PTR) and a receiver (PCR);
said UCD comprises a transmitter (CTR) and a receiver (CCR);
said PTR is configured to communicate with said CCR; and
said CTR is configured to communicate with said PCR.

12. The bioenergy storage and management system of claim 1 wherein said SEGU further comprises:
(a) electric generator to convert said biogas into said electrical power; and
(b) transformer configured to electrically couple output from said electric generator to said ETG or to an energy storage device.

13. The bioenergy storage and management system of claim 1 wherein said SEGU further comprises:
(a) electric generator to convert said biogas into said electrical power; and
(b) transformer configured to electrically couple output from said electric generator to a user transmission line (UTL).

14. The bioenergy storage and management system of claim 1 wherein said ETG is configured to be coupled to said SEGU and an alternate renewable generation unit (AEGU).

15. The bioenergy storage and management system of claim 1 wherein said BCU is configured to instantaneously couple said SEGU to said ETG.

16. The bioenergy storage and management system of claim 1 wherein said BCU is configured to schedule coupling of said SEGU to said ETG.

17. The bioenergy storage and management system of claim 1 wherein said BCU is configured to calculate available electrical power (AEP) based on measured quality and quantity of said stored biogas in said BSU, and efficiency of said SEGU.

18. A bioenergy management and storage method, said method operating in conjunction with said bioenergy management and storage system, said system comprising:
(a) biogas generation unit (BGU);
(b) biogas storage unit (BSU);
(c) stored energy electric generation unit (SEGU); and
(d) biogas control unit (BCU);
wherein
said BGU is configured to produce biogas;
said BGU is configured to transfer said biogas to said BSU;
said BSU is configured to store an amount of said biogas needed for peak demand;
said BSU is configured to transfer said biogas to said SEGU;
said SEGU is configured to generate electric power with said transferred biogas;
said BCU is configured to monitor the status of said BGU and said BSU;
said BCU is configured to control the operation of said BGU and said BSU;
said BCU is configured to control electrical coupling of said SEGU to an electric transmission grid (ETG); and
said BCU is configured to initiate said SEGU in response to a remote request for on demand power from an utility company, an independent system operator, a utility intermediary entity, from an energy storage device or from an onsite consumer;
wherein said method comprises the steps of:
(1) with said BCU, waiting for a request for electrical power (REP) indicating quantity (power level and duration) from a utility company;
(2) with said BCU, acknowledging said REP to said utility company;
(3) with said BCU, calculating available electrical energy and power (AEP) from said stored biogas;
(4) with said BCU, determining if said AEP is greater than 0, and if so, proceeding to step (7);
(5) with said BCU, responding with non-availability to said utility company;
(6) with said BGU, generating biogas and proceeding to said step (1);
(7) with said BCU, responding with said AEP quantity to said utility company;

(8) with said utility company, sending authorization to said BCU, for a negotiated electrical power (NEP) that is less than or equal to said AEP;

(9) with said BCU, determining if said NEP is required instantaneously, and if not, proceeding to step (11);

(10) with said BCU, connecting said SEGU to said ETG, transmitting said NEP and proceeding to said step (1); and

(11) with said BCU, connecting said SEGU to the ETG at a scheduled time, transmitting said NEP and proceeding to said step (1).

19. The bioenergy storage and management method of claim 18 wherein said BGU further comprises:
   (a) manure processing unit (MPU); and
   (b) anaerobic digester unit (ADU);
   wherein
   said MPU is configured to process manure;
   said MPU is configured to supply said processed manure to said ADU;
   said ADU is configured to produce said biogas using an Anaerobic Digestion Process (ADP);
   said ADU is configured to produce an effluent using said ADP; and
   said ADU is configured to transfer said biogas to said BSU.

20. The bioenergy storage and management method of claim 19 wherein said ADU is further configured to transfer said biogas to said SEGU.

21. The bioenergy storage and management method of claim 19 wherein said ADU is further configured to store said biogas.

22. The bioenergy storage and management method of claim 19 wherein said ADU is further configured to transfer said effluent to an effluent processing unit (EPU) to produce a fertilizer.

23. The bioenergy storage and management method of claim 18 wherein said communication further comprises:
   (a) producer communication device (PCD);
   (b) utility communication device (UCD); and
   (c) utility control unit (UCU);
   wherein
   said PCD is configured to permit remote control and monitoring of said BCU;
   said PCD is configured to communicate with said UCD;
   said UCD is configured to communicate with said PCD under control of said UCU; and
   said UCU is configured to permit remote control and monitoring of said BCU via data transferred to and from said PCD.

24. The bioenergy storage and management method of claim 23 wherein:
   said PCD comprises a transmitter (PTR) and a receiver (PCR);
   said UCD comprises a transmitter (CTR) and a receiver (CCR);
   said PTR is configured to communicate with said CCR; and
   said CTR is configured to communicate with said PCR.

25. The bioenergy storage and management method of claim 18 wherein said SEGU further comprises:
   (a) electric generator to convert said biogas into said electrical power; and
   (b) transformer configured to electrically couple output from said electric generator to said ETG.

26. The bioenergy storage and management system of claim 18 wherein said SEGU further comprises:
   (a) electric generator to convert said biogas into said electrical power; and
   (b) transformer configured to electrically couple output from said electric generator to a user transmission line (UTL).

27. The bioenergy storage and management system of claim 18 wherein said ETG is configured to be coupled to said SEGU and an alternate renewable generation unit (AEGU).

28. The bioenergy storage and management method of claim 18 wherein said BCU is configured to instantaneously couple said SEGU to said ETG.

29. The bioenergy storage and management method of claim 18 wherein said BCU is configured to schedule coupling of said SEGU to said ETG.

30. The bioenergy storage and management method of claim 18 wherein said BCU is configured to calculate available electrical power (AEP) based on measured quality and quantity of said stored biogas in said BSU, and efficiency of said SEGU.

* * * * *